US012678171B2

(12) United States Patent 
Kubota et al.

(10) Patent No.: US 12,678,171 B2 
(45) Date of Patent: Jul. 14, 2026

(54) HEMOSTATIC DEVICE

(71) Applicant: TERUMO KABUSHIKI KAISHA, Tokyo (JP)

(72) Inventors: Shuji Kubota, Fuji (JP); Kohei Watanabe, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 434 days.

(21) Appl. No.: 18/304,399

(22) Filed: Apr. 21, 2023

(65) Prior Publication Data

US 2023/0255641 A1 Aug. 17, 2023

Related U.S. Application Data

(63) Continuation of application No. PCT/JP2021/039234, filed on Oct. 25, 2021.

(30) Foreign Application Priority Data

Oct. 26, 2020 (JP) ................................. 2020-178745

(51) Int. Cl. 
*A61B 17/135* (2006.01)

(52) U.S. Cl. 
CPC .................................. *A61B 17/135* (2013.01)

(58) Field of Classification Search 
CPC .. A61B 17/135; A61B 17/1355; A61M 39/06; A61M 39/10; A61M 2039/066; 
(Continued)

(56) References Cited

U.S. PATENT DOCUMENTS

2006/0167492 A1* 7/2006 Prince .................... A61B 5/702 
600/420 
2015/0032063 A1 1/2015 Thorne 
(Continued)

FOREIGN PATENT DOCUMENTS

CN 202027653 U 11/2011 
CN 104414702 A 3/2015 
(Continued)

OTHER PUBLICATIONS

International Search Report (PCT/ISA/210) with translation and Written Opinion (PCT/ISA/237) mailed on Dec. 14, 2021 by the Japanese Patent Office as the International Searching Authority for International Application No. PCT/JP2021/039234. (8 pages).

(Continued)

*Primary Examiner* — Martin T Ton 
(74) *Attorney, Agent, or Firm* — BUCHANAN INGERSOLL & ROONEY PC

(57) ABSTRACT

A hemostatic device capable of performing decompression operation of an inflatable member and a reinjection operation of a fluid into the inflatable member without requiring a dedicated instrument includes an inflatable member configured to compress a puncture site, a band and a hook-and-loop fastener that function as a securing member to secure the inflatable member to the puncture site, and an injection member to inject fluid into a lumen of the inflatable member. The injection member includes a connector portion for injecting fluid, a main body portion including a tube connecting the connector portion and the inflatable member lumen, and a control unit that controls fluid flow through a lumen of the injection member. The control unit includes a first valve member, a second valve member located closer to the inflatable member than the first valve member, and a (Continued)

fluid storage portion located between the first and second valve members.

20 Claims, 28 Drawing Sheets

(58) Field of Classification Search
CPC .. A61M 2039/2493; A61M 2039/2433; A61M 2039/242; A61M 2039/263
See application file for complete search history.

(56) References Cited

U.S. PATENT DOCUMENTS

| | | | | |
|---|---|---|---|---|
| 2017/0086855 A1* | 3/2017 | Wada | ................... | A61B 17/135 |
| 2019/0133605 A1* | 5/2019 | Hazama | ........... | A61B 17/12009 |
| 2021/0236141 A1* | 8/2021 | Brikman | ............. | A61B 17/135 |
| 2023/0012280 A1* | 1/2023 | Hoffman | ............. | A61B 17/135 |

FOREIGN PATENT DOCUMENTS

| | | |
|---|---|---|
| CN | 109288567 A | 2/2019 |
| JP | 2011509099 A | 3/2011 |
| JP | 2013042859 A | 3/2013 |
| JP | 2019-136351 A | 8/2019 |
| WO | 2015199024 A1 | 12/2015 |
| WO | 2018/005611 A1 | 1/2018 |
| WO | 2019/159639 A1 | 8/2019 |
| WO | WO-2021238510 A1 * | 12/2021 ........... A61B 17/135 |

OTHER PUBLICATIONS

Extended European Search Report dated Mar. 1, 2024, issued in corresponding European Application No. 21886118.5. (9 pages).
English Translations of the International Search Report (Form PCT/ISA/210) and the Written Opinion of the International Searching Authority (Form PCT/ISA/237) issued Dec. 14, 2021, by the Japan Patent Office in corresponding International Application No. PCT/JP2021/039234. (5 pages).
Office Action (Notice of Reasons for Refusal) issued on Jul. 15, 2025, in corresponding Japanese Patent Application No. 2022-559109 and machine English translation of the Office Action. (10 pages).
Office Action/Search Report (The First Office Action) issued on Dec. 12, 2025, in corresponding Chinese Patent Application No. 202180070482.6 and machine English translation of the Office Action/Search Report. (14 pages).

* cited by examiner

HEMOSTATIC DEVICE

CROSS-REFERENCES TO RELATED APPLICATIONS

This application is a continuation of International Patent Application No. PCT/JP2021/039234 filed on Oct. 25, 2021, which claims priority to Japanese Patent Application No. 2020-178745 filed on Oct. 26, 2020, the entire content of both of which is incorporated herein by reference.

TECHNOLOGICAL FIELD

The present invention generally relates to a hemostatic device for stopping bleeding by compressing a puncture site of a patient.

BACKGROUND DISCUSSION

In recent years, percutaneous treatment and examination have been performed in which a blood vessel of an arm, a leg, or the like, is punctured, an introducer sheath is introduced into a puncture site, and a medical instrument such as a catheter is delivered to a lesion through a lumen of the introducer sheath. In a case where such treatment, examination, and the like, are performed, an operator (hereinafter, simply referred to as an "operator") such as a doctor needs to stop bleeding at the puncture site after removing the introducer sheath. In order to stop bleeding, there is known a hemostatic device including: securing means for securing a band body to be wound around a limb such as an arm or a leg in a state where the band body is wound around the limb; and an inflatable member that is connected to the band body and inflates by a fluid being injected to compress a puncture site.

In such a hemostatic device, if the inflated inflatable member continues to strongly compress the puncture site and the blood vessels and nerves around the puncture site for a long period, there is a possibility of causing numbness and pain or occluding the blood vessels. In order to prevent blood vessel occlusion, and the like, in general, after inflating the inflatable member, the operator periodically connects a dedicated instrument such as a syringe to the hemostatic device, discharges the fluid from the inflatable member according to a predetermined decompression protocol and performs decompression operation to reduce an internal pressure of the inflatable member, thereby reducing compressive force acting on the puncture site over time.

However, in such a hemostatic device, it is necessary to periodically connect a dedicated instrument such as a syringe to the hemostatic device, which may increase labor of the operator. In addition, if the dedicated instrument is lost during the decompression operation, there is a possibility that the decompression operation of the inflatable member cannot be performed.

International Patent Application Publication No. 2015/199024 (WO 2015/199024 A) discloses a hemostatic device including a pressure adjusting portion connected in communication with an inflatable member in order to perform decompression adjustment of the inflatable member without using a dedicated instrument such as a syringe in decompression operation of the inflatable member. The pressure adjusting portion includes a main body container portion connected in communication with the inflatable member and having a plurality of fluid through holes for releasing part of the fluid contained in the inflatable member. In addition, the pressure adjusting portion includes: a slide member that is attached to the main body container portion and moves along the main body container portion to open the fluid through holes at every plurality of stages from a state where the fluid through holes are closed; and a moving body that moves in the main body container portion and sequentially closes air through holes opened by the slide member at every plurality of stages. In the hemostatic device described in International Patent Application Publication No. 2015/199024, when a site of a limb where bleeding is to be stopped is pressed, the operator can easily and arbitrarily adjust a compressive force to the site where bleeding is to be stopped according to a state of a patient, so that it is possible to reduce labor of the operator to adjust the compressive force.

SUMMARY

The hemostatic device described in International Patent Application Publication No. 2015/199024 includes the pressure adjusting portion for performing decompression adjustment of the inflatable member, and thus, an amount of decompression by the decompression operation can be adjusted according to a state of a patient without using a dedicated instrument such as a syringe. However, the pressure adjusting portion is constituted by a separate member which is further branched from and connected to an injection portion communicating with the inflatable member, and thus, the pressure adjusting portion may become an obstacle when the hemostatic device is operated.

In addition, the hemostatic device described in International Patent Application Publication No. 2015/199024 also performs operation of reinjecting a fluid according to a hemostatic state of a puncture site when decompression operation is performed. However, in this hemostatic device, in a case where the operation of reinjecting a fluid is performed, the fluid needs to be reinjected using a dedicated instrument such as a syringe. As described above, in view of operability of the operator, the hemostatic device described in International Patent Application Publication No. 2015/199024 has room for improvement in a structure for performing decompression operation of the inflatable member and operation of reinjecting a fluid.

The hemostatic device disclosed here is capable of performing decompression operation of an inflatable member and operation of reinjecting a fluid into the inflatable member by simple operation without using a dedicated instrument separate from the hemostatic device and is capable of reducing labor of the decompression operation and the operation of reinjecting a fluid by the operator.

A hemostatic device according to the present embodiment disclosed by way of example includes: an inflatable member configured to compress a puncture site of a patient; a securing member configured to secure the inflatable member to the puncture site of the patient; and an injection member configured to be able to inject a fluid into a lumen of the inflatable member, in which the injection member includes a connector portion for injecting the fluid; a main body portion that connects the connector portion and the lumen of the inflatable member, and a control unit that controls flow of the fluid through a lumen of the injection member, and the control unit includes a first valve member, a second valve member located closer to the inflatable member than the first valve member, and a fluid storage portion located between the first valve member and the second valve member.

According to at least one embodiment, after an operator injects a fluid into an inflatable member, the operator can perform decompression operation and operation of reinjecting a fluid to the inflatable member by simple operation, so that it is possible to reduce labor of the decompression operation and the reinjection operation by the operator. The injection member of the hemostatic device includes a control unit having a first valve member, a second valve member, and a fluid storage portion positioned between the first valve member and the second valve member. By operating the first valve member and the second valve member, the control unit can store a predetermined amount of fluid in the fluid storage portion and reinject gas stored in the fluid storage portion into the inflatable member. In other words, by storing a predetermined amount of gas in the fluid storage portion, the control unit can release a predetermined amount of gas from the inflatable member or reinject a predetermined amount of gas into the inflatable member. Thus, when the inflatable member is decompressed, the operator operates open/closed states of the first valve member and the second valve member to cause part of the fluid stored in the inflatable member to flow to the fluid storage portion, so that the fluid can be discharged from the inflatable member. In addition, when a fluid is reinjected into the inflatable member, the operator can inject the fluid into the inflatable member by operating the open/closed states of the first valve member and the second valve member to cause a predetermined amount of the fluid stored in the fluid storage portion to flow into the inflatable member. As described above, the hemostatic device disclosed here can perform decompression operation and operation of reinjecting a fluid to the inflatable member by simple operation without using a dedicated instrument separate from the hemostatic device. Thus, the hemostatic device can reduce labor of discharge operation and reinjection operation on the inflatable member by the operator.

According to another aspect, a hemostatic device comprises an inflatable member that is inflatable by way of fluid flowing into an interior of the inflatable member, and a band to which the inflatable member is connected, wherein the band includes first and second portions that are engageable with one another when the band is in a wrapped state on the patient to secure the band on the patient and position the inflatable member to apply a compression force to the puncture site when the inflatable member is inflated. A first valve and a second valve are spaced apart from one another, and a fluid storage is positioned between the first valve and the second valve. The fluid storage includes an interior, and the first valve and the second valve are switchable between an open state and a closed state. The first valve is connected to the fluid storage container and the inflatable member so that when the first valve is in the open state the first valve permits communication between the interior of the inflatable member and the interior of the fluid storage and so that when the first valve is in the closed state communication between the interior of the inflatable member and the interior of the fluid storage is blocked by the first valve. At least one of the first valve and the second valve comprises one valve body and an other valve body that are connected to each other by a connection member, with the connection member allowing relative movement between the one valve body and the other valve body to switch the at least one of the first valve and the second valve between the open state and the closed state.

In accordance with another aspect, a hemostatic device comprises an inflatable member that is inflatable by way of fluid flowing into an interior of the inflatable member, and a band to which the inflatable member is connected. The band is wrappable around a portion of the patient in a wrapped state to position the inflatable member relative to a puncture site of the patient. The band includes first and second portions that are engageable with one another when the band is in the wrapped state on the patient to secure the band on the patient and position the inflatable member to apply a compression force to the puncture site when the inflatable member is inflated. A first valve and a second valve are spaced apart from one another and are axially movable relative to one another, and a fluid storage is positioned between the first valve and the second valve. The fluid storage is joined to the first valve and the second valve so that an interior of the fluid storage is sealed, and each of the first valve and the second valve is switchable between an open state in which fluid flow is permitted and a closed state in which fluid flow is prevented. The first valve has one end in communication with the interior of the inflatable member and an opposite end in communication with the interior of the fluid storage, and the second valve has one end connectable to a source of the fluid and an opposite end in communication with the interior of the fluid storage. The fluid storage that is positioned between the first valve and the second valve is constructed to permit the first valve and the second valve to axially movable relative to one another.

BRIEF DESCRIPTION OF THE DRAWINGS

FIG. 1 is a plan view illustrating a configuration of a hemostatic device according to the present embodiment.

FIG. 3 is an enlarged partial cross-sectional view of a periphery of an injection member in the hemostatic device according to the present embodiment.

FIG. 16A is a view illustrating a configuration of a first valve member including a first securing and holding member in a hemostatic device according to a second modification.

DETAILED DESCRIPTION

Set forth below with reference to the accompanying drawings is a detailed description of embodiments/modifications of a hemostatic device representing examples of the hemostatic device disclosed here. The embodiments/modifications illustrated herein are set forth to embody technical idea of the disclosure here and do not limit the present invention. Furthermore, other embodiments, modification, examples, operation techniques, and the like, that can be implemented by those skilled in the art without departing from the gist of the disclosed hemostatic device are all included in the scope and gist of the disclosure here and are encompassed in the invention described in the claims and the scope of equivalents thereof.

Moreover, for convenience of illustration and ease of understanding, the accompanying drawings may be schematically represented by changing a scale, an aspect ratio, a shape, and the like, from actual ones as appropriate, and are merely examples, and do not limit the interpretation of the present invention.

In the present specification, ordinal numerals such as "first" and "second" will be given, but are used for convenience and do not define any order unless otherwise specified.

Figure 9:
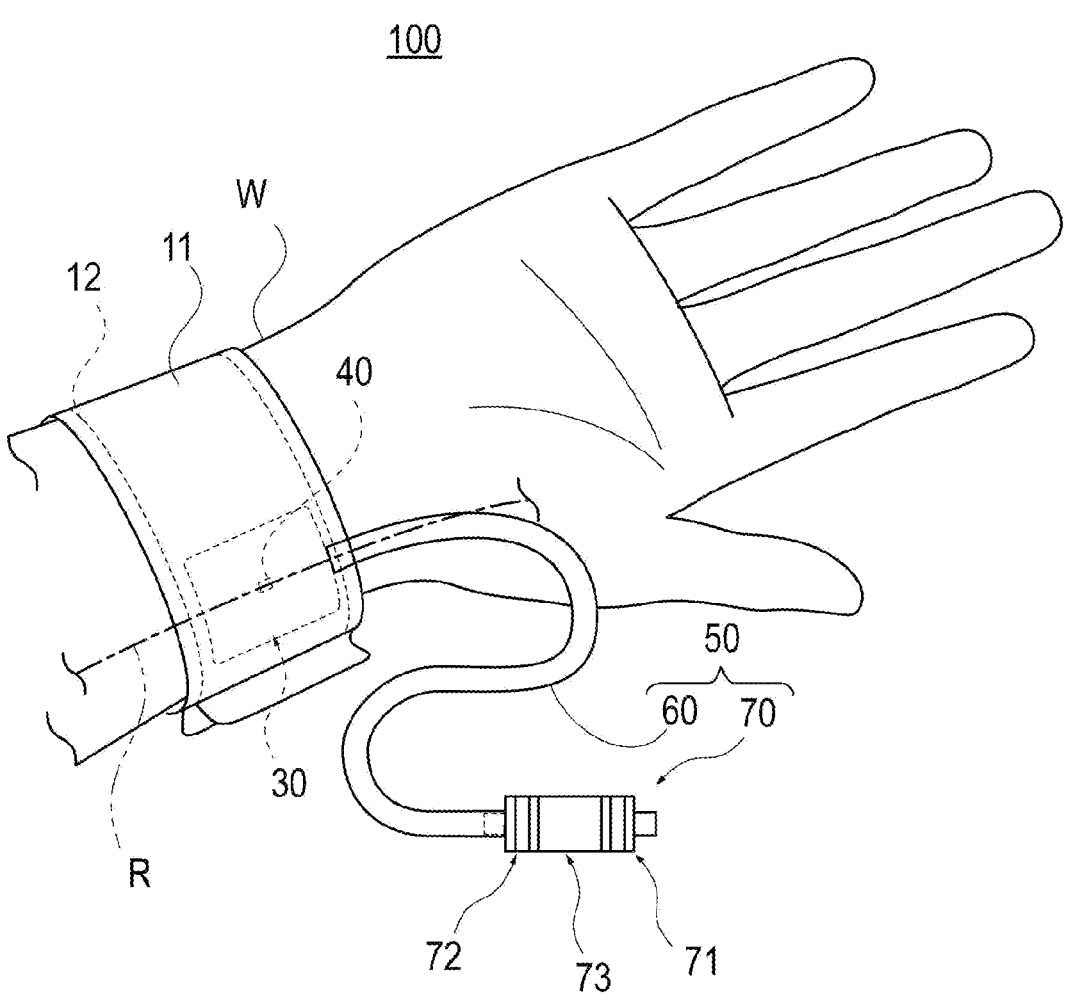
FIG. 9 is a perspective view illustrating a state in which the hemostatic device according to the present embodiment is worn.

As illustrated in FIG. 9, a hemostatic device 100 according to one disclosed embodiment is used for stopping bleeding at a puncture site of a patient's wrist W after removing a device such as an introducer sheath placed at the puncture site formed in a radial artery R for the purpose of inserting a catheter, or the like, for treatment, examination, or the like, into a blood vessel. The content of specific procedure, treatment procedure, and the like, using the hemostatic device 100 according to an embodiment are representative examples, and do not specify or limit hemostatic device described here.

<Configuration>

Figure 1:
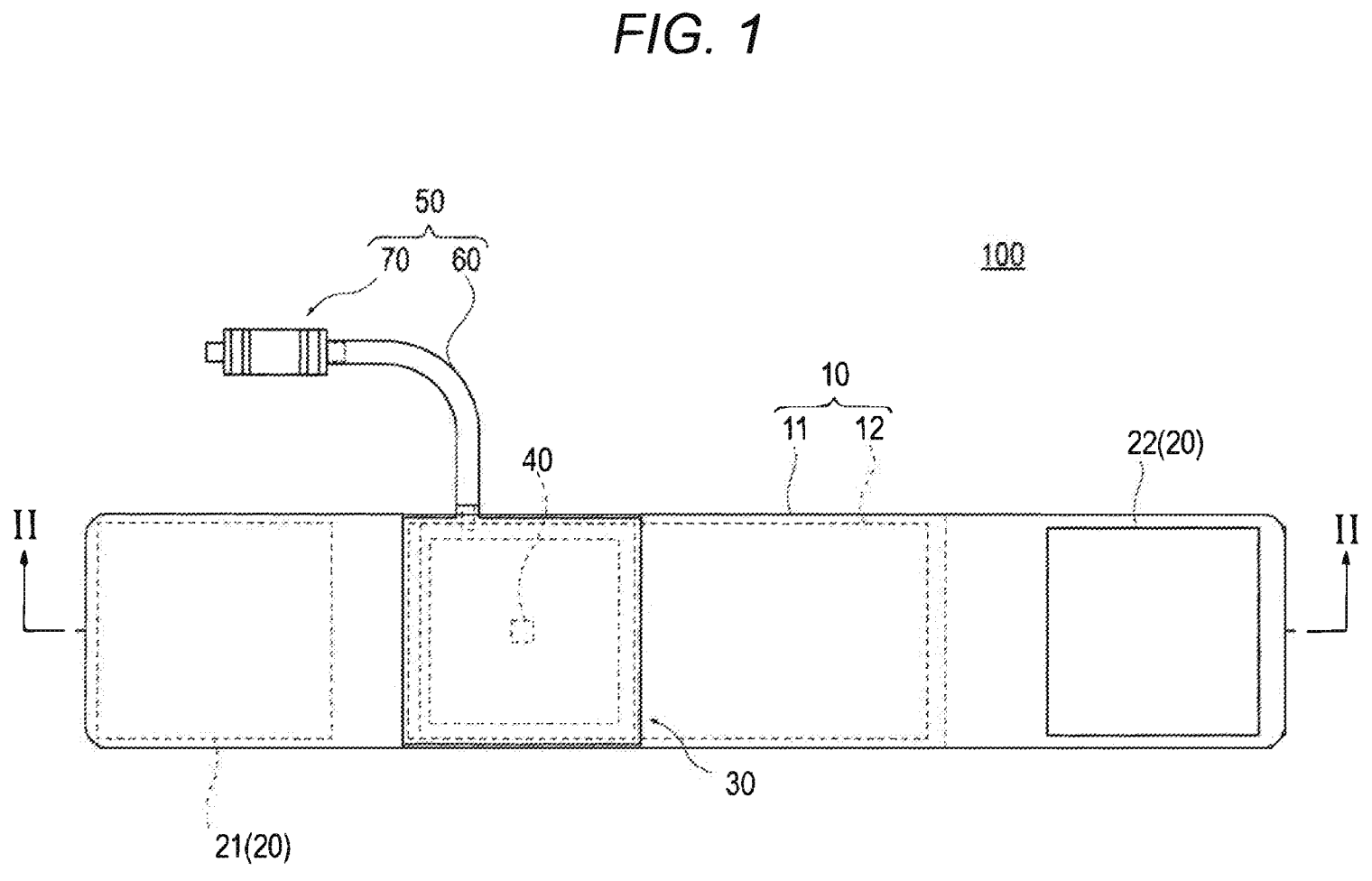
Figure 2:
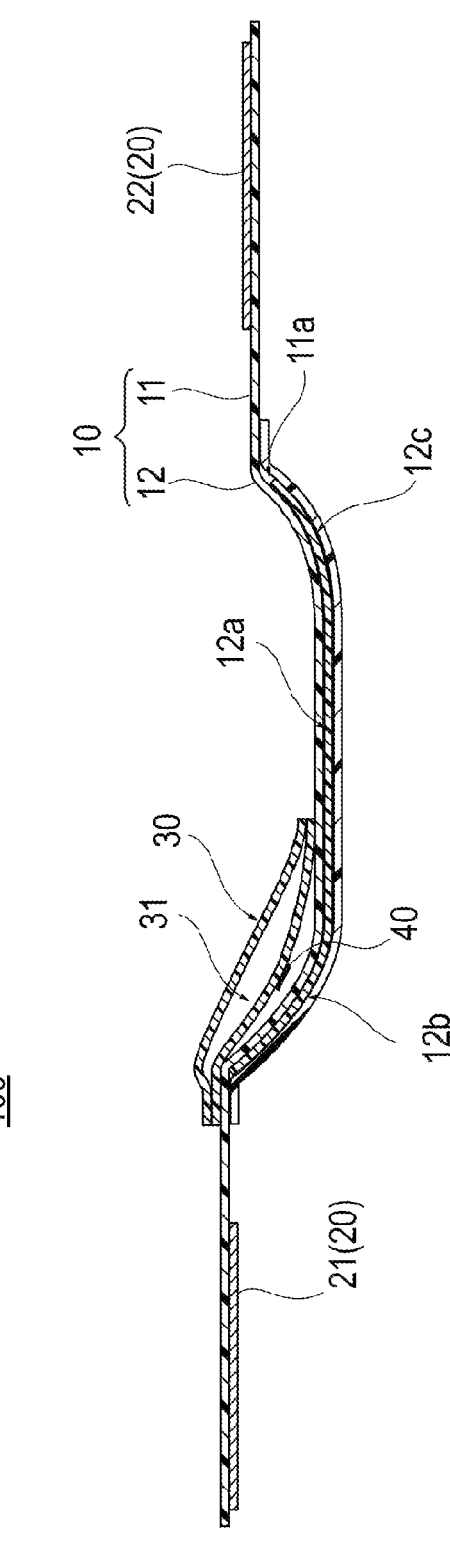
FIG. 2 is a schematic cross-sectional view taken along the section line Il-Il in FIG. 1.

First, the hemostatic device 100 according to the present embodiment will be described with reference to FIGS. 1 to 8C as appropriate. As illustrated in FIG. 1 and FIG. 2, the hemostatic device 100 generally includes a band body (band) 10 to be wound around a wrist W, a hook-and-loop fastener 20 for securing the band body 10 in a state where the band body 10 is wound around the wrist W, an inflatable member 30 that inflates by injection of a fluid to compress a puncture site, a marker 40 for aligning the inflatable member 30 with the puncture site, and an injection member 50 capable of injecting a fluid into the inflatable member 30. In the hemostatic device 100, the band body 10 and the hook-and-loop fastener 20 function as a "securing member" for securing the inflatable member 30 to the puncture site.

The fluid to be injected into the inflatable member 30 is not particularly limited as long as it can be injected and discharged into and from the inflatable member 30, for example, gas such as air or a liquid such as purified water or physiological saline. In the present embodiment, gas (air) that is easier to handle and easier to inject and discharge than a liquid is used as the fluid.

In the present specification, when the band body 10 is wound around the wrist W, a side (attachment surface side) of the band body 10 facing a body surface of the wrist W is referred to as an "inner surface side", and the opposite side is referred to as an "outer surface side".

The band body 10 includes a belt 11 formed of a band-shaped member having flexibility, and a support plate 12 having higher hardness than the belt 11.

As illustrated in FIG. 9, the belt 11 is wound around an outer circumference of the wrist W so as to go or wrap substantially one round around the wrist. A support plate holding portion 11a that holds the support plate 12 is formed in a central portion of the belt 11. The support plate holding portion 11a may be formed as a doubled layer by joining separate belt-shaped members to the outer surface side (or the inner surface side) by a method such as fusion (thermal fusion, high-frequency fusion, ultrasonic fusion, etc.) or adhesion (adhesion using an adhesive or a solvent) and holds the support plate 12 inserted into a gap between the layers.

A male side (or female side) 21 of the hook-and-loop fastener 20 generally called a Magic Tape® (registered trademark), or the like, is disposed on the outer surface side of a portion near a left end in FIG. 1 of the belt 11, and a female side (or male side) 22 of the hook-and-loop fastener 20 is disposed on the inner surface side of a portion near a right end in FIG. 1 of the belt 11. As illustrated in FIG. 9, the belt 11 is wound around the wrist W, and the male side 21 and the female side 22 are joined, whereby the band body 10 is worn on the wrist W. The means or mechanism for securing the band body 10 wound around the wrist W is not limited to the hook-and-loop fastener 20 and may be, for example, a snap, a button, a clip, or a frame member through which the end portion of the belt 11 passes.

A constituent material from which the belt 11 may be fabricated is not particularly limited as long as it has flexibility. Examples of such a material include polyolefins such as polyvinyl chloride, polyethylene, polypropylene, polybutadiene, and ethylene-vinyl acetate copolymer (EVA), polyesters such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any combination thereof (blend resin, polymer alloy, laminate, and the like).

In addition, at least a portion of the belt 11 overlapping the inflatable member 30 is preferably substantially transparent, but is not limited to being transparent and may be translucent or colored transparent. As a result, the puncture site can be visually recognized from the outer surface side, so that the marker 40 can be easily aligned with the puncture site.

As illustrated in FIG. 2, the support plate 12 is held by the belt 11 by being inserted or positioned between the double-formed support plate holding portions 11a of the belt 11. The support plate 12 has a plate shape in which at least part thereof is curved toward the inner surface side (attachment surface side). The support plate 12 is made of a material more rigid than the belt 11 and maintains a substantially constant shape.

The support plate 12 has a shape elongated in a longitudinal direction of the belt 11. A central portion 12a in the longitudinal direction of the support plate 12 has a flat plate shape with little curvature, a first curved portion 12b on one side of the central portion 12a (left side in FIG. 2) and a second curved portion 12c on the opposite side of the central portion 12a (right side in FIG. 2). The first and second curved portions 12b, 12c curved toward the inner surface side and along the longitudinal direction of the belt 11 (circumferential direction of the wrist W) are formed.

Examples of a constituent material from which the support plate 12 may be fabricated include an acrylic resin, polyolefin such as polyvinyl chloride (particularly, hard polyvinyl chloride), polyethylene, polypropylene and polybutadiene, polyester such as polystyrene, poly-(4-methylpentene-1), polycarbonate, an ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET) and polybutylene terephthalate (PBT), and a fluorine-based resin such as a butadiene-styrene copolymer, aromatic or aliphatic polyamide and polytetrafluoroethylene.

As with the belt 11, a portion of the support plate 12 overlapping the inflatable member 30 is preferably substantially transparent, but is not limited to being transparent and may be translucent or colored transparent. As a result, the puncture site can be reliably visually recognized from the outer surface side, so that the marker 40 can be easily aligned with the puncture site. The support plate 12 may have a shape curved over the entire length without having a flat plate-like portion like the central portion 12a.

The inflatable member 30 is connected to the band body 10. The inflatable member 30 inflates by a fluid being injected to compress the puncture site of the wrist W.

As illustrated in FIG. 2, on the inner surface side of the band body 10, the inflatable member 30 is positioned so as to overlap with one end side in the longitudinal direction of the support plate 12 held by the band body 10. In other words, in the illustrated configuration, the inflatable member 30 is positioned so as to overlap a part of the support plate 12, namely the part in the vicinity between the first curved portion 12b and the central portion 12a on the left end side in FIG. 2 of the support plate 12. Thus, when an inflatable space 31 is inflated, the support plate 12 prevents the inflatable member 30 from inflating in a direction in which the inflatable member 30 is separated from the body surface of the wrist W, and a compressive force of the inflatable member 30 is concentrated on the wrist W side. This makes it possible for the inflatable member 30 to suitably apply a compressive force to the puncture site.

In a case where the inflatable member 30 is positioned so as to overlap with one end side in the longitudinal direction of the support plate 12, the first curved portion 12b located on one side of the central portion 12a in the longitudinal direction of the support plate 12 is longer in the longitudinal direction than the second curved portion 12c located on the opposite side of the central portion 12a in the longitudinal direction of the support plate 12. This results in making it possible to reduce a risk that the second curved portion 12c of the support plate 12 comes into contact with the wrist W and pain such as aching pain occurs when the hemostatic device 100 is worn on the wrist W and the inflatable member 30 inflates.

A constituent material from which the inflatable member 30 may be fabricated is not particularly limited as long as it is a material having flexibility, and for example, the same constituent material as the above-described constituent material of the belt 11 can be used. In addition, the inflatable member 30 is preferably made of the same material or the same kind of material as the belt 11. Accordingly, the inflatable member 30 can be easily joined to the belt 11 by fusion.

For example, as illustrated in FIG. 2, the inflatable member 30 is constituted as a bag-shaped member in which two sheets made of the above-described materials are overlapped and the peripheral edges of the overlapped sheets are bonded or fused. By this means, the inflatable space 31 is formed between the two sheets. The configuration of the inflatable member 30 is not particularly limited as long as it can inflate by a fluid being injected. For example, the inflatable member 30 may be constituted by a bag-shaped member obtained by bending (folding) one sheet and bonding or fusing an edge portion or a balloon-shaped member having no edge portion. In addition, the inflatable member 30 may be configured to have an outer shape formed in a quadrangular shape in a plan view in a state where it is not inflated as illustrated in FIG. 1, for example. The inflatable member 30 may have an outer shape such as a circle, an ellipse, or a polygon in a plan view in a state where it is not inflated.

When the inflatable member 30 is inflated (expanded), a front cylindrical portion of a syringe S, which is a tool for fluid injection, is inserted into a connector portion (as an example, a first protruding portion 71g of a first valve body 71a to be described later) of the injection member 50, and a pusher of the syringe S is pushed to inject gas in the syringe S into the inflatable member 30 via the injection member 50. The operation of injecting gas into the inflatable member 30 will be described later in detail.

Similar to the belt 11 and the support plate 12, the inflatable member 30 is preferably substantially transparent, but is not limited to being transparent and may be translucent or colored transparent. As a result, the operator can visually recognize the puncture site from the outer surface side and can easily align the marker 40 with the puncture site.

As illustrated in FIGS. 1 and 2, the marker 40 is provided substantially at the center of the inflatable member 30 on a side facing the band body 10. By providing such a marker 40 on the inflatable member 30, the inflatable member 30 can be easily aligned with respect to the puncture site, so that positional displacement of the inflatable member 30 is prevented. In addition, the marker 40 is provided on the surface of the inflatable member 30 facing the band body 10, and thus, the marker 40 does not directly contact the puncture site. A position where the marker 40 is provided is not particularly limited as long as the inflatable member 30 can be aligned with the puncture site. Thus, the marker 40 may be provided on the side facing the wrist W in the inflatable member 30. In this event, the marker 40 is preferably provided on the inner surface of the inflatable member 30 so as not to directly contact the puncture site.

A shape of the marker 40 is not particularly limited, and examples thereof include a circle, a polygon such as a triangle and a quadrangle, and in the present embodiment, the shape is a quadrangle.

A size of the marker 40 is not particularly limited, but for example, in a case where the shape of the marker 40 is a quadrangle, a length of one side is preferably in a range of 1 to 4 mm. If the length of one side is 5 mm or more, the size of the marker 40 is larger than the size of the puncture site, so that it is difficult to align the central portion of the inflatable member 30 with the puncture site.

The material of the marker 40 is not particularly limited, and examples thereof include an oily colorant such as an ink, a resin obtained by kneading a dye, and the like.

The color of the marker 40 is not particularly limited as long as the inflatable member 30 can be aligned with the puncture site, but is preferably a green color. By making the color green, the marker 40 can be easily visually recognized on blood or skin, so that it is easier to align the inflatable member 30 with the puncture site.

In addition, the marker 40 is preferably translucent or colored transparent. As a result, the puncture site can be visually recognized from the outer surface side of the marker 40.

A method for providing the marker 40 on the inflatable member 30 is not particularly limited, and examples thereof include a method in which the marker 40 is printed on the inflatable member 30, a method in which an adhesive is applied to one surface of the marker 40 and attached to the inflatable member 30, and the like.

The injection member 50 is a portion for injecting gas into the inflatable member 30 and is connected to the inflatable member 30 as illustrated in FIG. 1.

Figure 3:
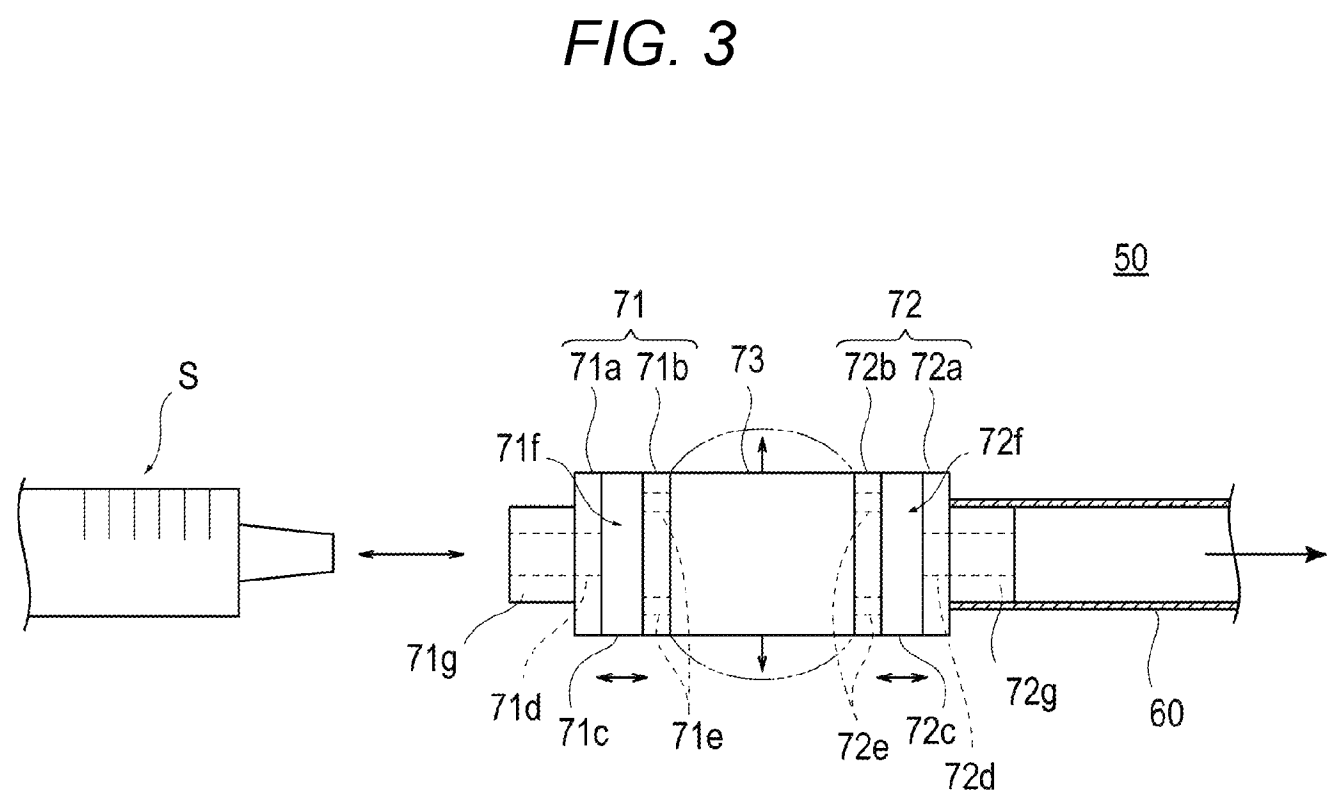

The injection member 50 includes a flexible tube 60 whose lumen communicates with the lumen of the inflatable member 30, and a control unit 70 which communicates with the lumen of the tube 60 and is disposed at the proximal portion of the tube 60. In the present embodiment, as illustrated in FIG. 3, the control unit 70 has a connector portion to which a tool for fluid injection (syringe S) can be connected in order to inject gas into the inflatable member 30. The connector portion may be configured by connecting another member to which a fluid injection tool (syringe S) can be connected to the first protruding portion 71g of the control unit 70. In the injection member 50, a "distal end (distal side)" refers to a side on which the fluid flows toward the inflatable member 30 (that is, the tube 60 side), and a "proximal end (proximal side)" refers to a side on which the fluid is discharged from the inflatable member 30 (that is, the first protruding portion 71g side of the first valve body 71a). In addition, in the injection member 50, a "long axis direction" is a direction of an axis extending in the longitudinal direction (direction from the proximal side to the distal side) of the injection member 50.

The tube 60 constitutes a main body portion of the injection member 50. The tube 60 is connected to and communicates with the lumen of the inflatable member 30 and allows the lumen of the inflatable member 30 to communicate with the outside. This allows the gas injected from the connector portion to flow to the inflatable space 31 of the inflatable member 30 via the control unit 70 and the tube 60. The gas stored in the inflatable space 31 can be discharged to the outside through the tube 60 and the control unit 70.

A distal portion of the tube 60 is connected to the inflatable member 30, and a proximal portion of the tube 60 is connected to the control unit 70. A connection position of the tube 60 with the inflatable member 30 is not particularly limited as long as the lumen of the tube 60 communicates with the inflatable space 31 of the inflatable member 30.

The control unit 70 controls flow of gas passing through the lumen of the injection member 50. In the control unit 70, one end portion forms the connector portion or is connected to the connector portion, and the other end portion is connected to the tube 60. In the present embodiment, as illustrated in FIG. 3, the control unit 70 includes a first protruding portion 71g that functions as the connector portion. Thus, the control unit 70 is connected to the tube 60 such that a portion other than the first protruding portion 71g that becomes the connector portion is located between the connector portion (first protruding portion 71g) and the inflatable member 30 and communicates with the lumen of the tube 60.

The control unit 70 includes a first valve member 71, a second valve member 72 located on the distal side (inflatable member 30 side) of the first valve member 71, and a fluid storage portion 73 located between the first valve member 71 and the second valve member 72. The first valve member 71 and the second valve member 72 include a securing and holding member 80 (first securing and holding member 81, second securing and holding member 82) for maintaining a closed state of each of the valve members 71 and 72.

The first valve member 71 includes a first valve body 71a located on the proximal side of the injection member 50 and a second valve body 71b disposed on the distal side in the long axis direction of the injection member 50 so as to face the first valve body 71a. The first valve body 71a and the second valve body 71b are connected by a first connection member 71c so as to be relatively movable (approaching and separating) along the long axial direction of the injection member 50. A state of the first valve member 71 can be switched between an open state (a state in which gas can flow) and a closed state (a state in which gas flow is blocked) by approaching or separating movement of the first valve body 71a and the second valve body 71b. The first valve member 71 includes a first securing and holding member 81 that holds the first valve body 71a and the second valve body 71b in a state of being in close contact with each other.

The first valve body 71a is made of a plate material provided with a first hole 71d that penetrates in a thickness direction and through which gas can flow. The first valve body 71a has a disk shape and includes a first protruding portion 71g on an end surface on the proximal side in the thickness direction. As an example, the first protruding portion 71g has a cylindrical shape having a lumen and extends on the proximal side in the long axis direction (axial direction) of the injection member 50. In the present embodiment, as described above, the first protruding portion 71g is mounted with a distal portion of a dedicated instrument such as the syringe S for injecting gas and functions as a "connector portion" for injecting gas.

The second valve body 71b is made of a plate material provided with a second hole 71e that penetrates in the thickness direction and through which gas can flow. In the present embodiment, the second valve body 71b has a disk shape similarly to the first valve body 71a. The second hole 71e allows a first flow space 71f formed by the first connection member 71c to communicate with a lumen of the fluid storage portion 73.

Shapes s of the first valve body 71a and the second valve body 71b are not limited to the disk shape, and the shapes viewed from the long axis direction side may be a polygon such as a triangle or a quadrangle.

Figure 4A:
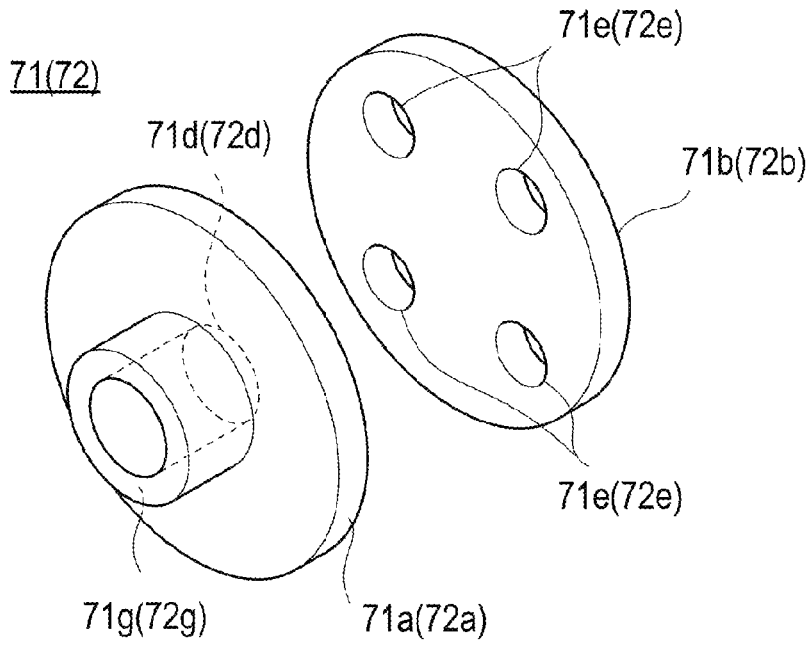
FIG. 4A is a view illustrating a state in which a first valve body (third valve body) and a second valve body (fourth valve body) constituting a first valve member (second valve member) of the hemostatic device according to the present embodiment are separated.
Figure 4B:
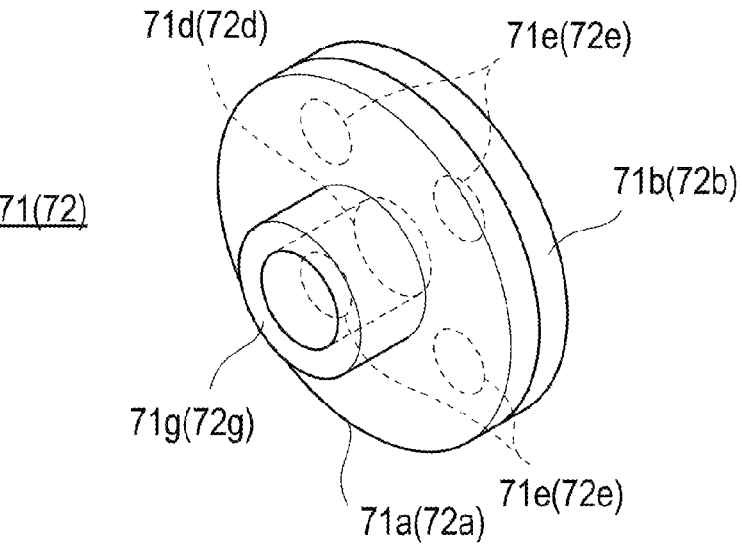
FIG. 4B is a conceptual diagram illustrating a state in which the first valve body (third valve body) and the second valve body (fourth valve body) constituting the first valve member (second valve member) of the hemostatic device according to the present embodiment are brought into close contact with each other.

FIGS. 4A and 4B illustrate an arrangement mode example of the first hole 71d provided in the first valve body 71a and the second hole 71e provided in the second valve body 71b. As illustrated in FIG. 4A, the first hole 71d is disposed in accordance with a position of the first protruding portion 71g so as to be communicable with the lumen of the first protruding portion 71g. The second hole 71e is disposed at a position not arranged in series with the first hole 71d. That is, the central axis of the second hole 71e is spaced outwardly of the central axis of the first hole 71d (i.e., not coaxial), and the second hole 71e is not aligned with the first hole 71d. In a state of FIG. 4A, gas can flow through the first valve member 71. As illustrated in FIG. 4B, when the end surface of the first valve body 71a and the end surface of the second valve body 71b are overlapped (that is, when the first valve body 71a is projected onto or in contact with the second valve body 71b), the first hole 71d and the second hole 71e are arranged at different positions. Thus, if the first valve body 71a and the second valve body 71b are secured by the first securing and holding member 81 in a state where they are in close contact with each other, the first hole 71d is closed by the end surface of the second valve body 71b, the second hole 71e is closed by the end surface of the first valve body 71a, and the flow of the gas is blocked. In other words, in a state of FIG. 4B, the first valve member 71 is in a state in which gas cannot flow. As described above, the first valve member 71 can control flow of the gas by closing or opening the first hole 71d and the second hole 71e by bringing the first valve body 71a and the second valve body 71b close to or away from each other. Thus, the first valve member 71 can easily switch the state between the open state and the closed state with a simple configuration. The first hole 71d and the second hole 71e may be closed or opened in a state where at least the first valve body 71a and the second valve body 71b are in close contact with each other, and the number of holes formed and the hole shape are not limited to the form illustrated in FIG. 4A.

The first connection member 71c is made of a flexible film material and connects the first valve body 71a and the second valve body 71b so as to be relatively movable along the long axis (axial) direction of the injection member 50. In a state of being joined to the first valve body 71a and the second valve body 71b, the first connection member 71c forms a first flow space 71f which is a sealed space through which gas can flow between the first valve body 71a and the second valve body 71b. Thus, when the gas flows between the first valve body 71a and the second valve body 71b, the gas is prevented from leaking from the first flow space 71f to the outside.

In the present embodiment, for example, as illustrated in FIG. 3, the film material constituting the first connection member 71*c* is joined to the vicinity of the outer peripheral end portion on the proximal side of the first valve body 71*a* and the vicinity of the outer peripheral end portion on the distal side of the second valve body 71*b*. However, the joining position of the film material constituting the first connection member 71*c* is not particularly limited as long as the film material is joined to the outer peripheral surfaces of the first valve body 71*a* and the second valve body 71*b*.

The second valve member 72 includes a third valve body 72*a* located on the distal side of the injection member 50 and a fourth valve body 72*b* disposed on the proximal side in the long axis (axial) direction of the injection member 50 so as to face the third valve body 72*a*. The third valve body 72*a* and the fourth valve body 72*b* are connected by the second connection member 72*c* so as to be relatively movable (approaching and separating) along the long axis (axial) direction of the injection member 50. A state of the second valve member 72 can be switched between an open state and a closed state by approaching or separating movement of the third valve body 72*a* and the fourth valve body 72*b*. The second valve member 72 includes a second securing and holding member 82 that holds the third valve body 72*a* and the fourth valve body 72*b* in a state of being in close contact with each other.

The third valve body 72*a* is made of a plate material provided with a third hole 72*d* through which gas can flow. The third valve body 72*a* has a disk shape and includes a second protruding portion 72*g* on the end surface on the distal side in the thickness direction. The second protruding portion 72*g* has a cylindrical shape having a lumen as an example and extends to the distal side in the long axis (axial) direction of the injection member 50. A tube 60 is connected to the second protruding portion 72*g*. As a result, the control unit 70 is connected to the inflatable member 30 via the tube 60 in a communicable manner.

The fourth valve body 72*b* is made of a plate material provided with a fourth hole 72*e* through which gas can flow. In the present embodiment, the fourth valve body 72*b* has a disk shape similarly to the third valve body 72*a*. The fourth hole 72*e* allows the second flow space 72*f* formed by the second connection member 72*c* to communicate with the lumen of the fluid storage portion 73.

The shapes of the third valve body 72*a* and the fourth valve body 72*b* are not limited to the disk shape as with the first valve body 71*a* and the second valve body 71*b*, and the shapes viewed from the long axis (axial) direction side may be a polygon such as a triangle or a quadrangle.

As illustrated in FIG. 4A, the third hole 72*d* is disposed in accordance with a position of the second protruding portion 72*g* so as to be communicable with the lumen of the second protruding portion 72*g*. The fourth hole 72*e* is disposed at a position not arranged in series with the third hole 72*d*. That is, the central axis of the fourth hole 72*e* is spaced outwardly of the central axis of the third hole 72*d*, and the fourth hole 72*e* is not capable of being aligned with the third hole 72*d*. In the state of FIG. 4A, gas can flow through the second valve member 72. As illustrated in FIG. 4B, when the end surface of the third valve body 72*a* and the end surface of the fourth valve body 72*b* are overlapped (that is, when the third valve body 72*a* is projected onto or in contact with the fourth valve body 72*b*), the third hole 72*d* and the fourth hole 72*e* are arranged at different positions. Thus, if the third valve body 72*a* and the fourth valve body 72*b* are secured by the second securing and holding member 82 in a state where they are in close contact with each other similarly to the first valve body 71*a* and the second valve body 71*b*, the third hole 72*d* is closed by the end surface of the fourth valve body 72*b*, the fourth hole 72*e* is closed by the end surface of the third valve body 72*a*, and the flow of gas is blocked. In other words, in the state of FIG. 4B, the second valve member 72 is in a state in which gas cannot flow. As described above, in the second valve member 72, the third valve body 72*a* and the fourth valve body 72*b* are brought close to or separated from each other to close or open the third hole 72*d* and the fourth hole 72*e*, whereby the flow of gas can be controlled. Thus, similarly to the first valve member 71, the second valve member 72 can easily switch a state between the open state and the closed state with a simple configuration. The third hole 72*d* and the fourth hole 72*e* may be closed or opened in a state where at least the third valve body 72*a* and the fourth valve body 72*b* are brought into close contact with each other, and the number of holes formed and the hole shape are not limited to those illustrated in FIG. 4.

The second connection member 72*c* is made of a flexible film material and connects the third valve body 72*a* and the fourth valve body 72*b* so as to be relatively movable along the long axis (axial) direction of the injection member 50. In a state of being joined to the third valve body 72*a* and the fourth valve body 72*b*, the second connection member 72*c* forms a second flow space 72*f* serving as a sealed space through which gas can flow between the third valve body 72*a* and the fourth valve body 72*b*. Thus, when the gas flows between the third valve body 72*a* and the fourth valve body 72*b*, the gas is prevented from leaking from the second flow space 72*f* to the outside.

In the present embodiment, for example, as illustrated in FIG. 3, the film material constituting the second connection member 72*c* is joined to the vicinity of the outer peripheral end portion on the distal side of the third valve body 72*a* and the vicinity of the outer peripheral end portion on the proximal side of the fourth valve body 72*b*. However, the joining position of the film material constituting the second connection member 72*c* is not particularly limited as long as the film material is joined to the outer peripheral surfaces of the third valve body 72*a* and the fourth valve body 72*b*.

The fluid storage portion 73 is a sealable space that is positioned between the first valve member 71 and the second valve member 72 and stores the gas flowing from the inflatable member 30. The gas stored in the inflatable member 30 flows into the fluid storage portion 73 by action of a pressure difference generated between an internal pressure of the inflatable space 31 of the inflatable member 30 and an internal pressure of the fluid storage portion 73 by predetermined operation on the second valve member 72 being performed. The fluid storage portion 73 has a volume capable of storing an amount of gas to be degassed (an amount of fluid to be discharged) according to a predetermined decompression protocol. The volume of the fluid storage portion 73 may be appropriately set according to the decompression protocol.

The fluid storage portion 73 may have a configuration capable of storing a predetermined amount of gas. Thus, the fluid storage portion 73 may be, for example, a balloon type made of an inflatable film material having more flexibility than the material of the main body portion (tube 60) or a tube type made of a material having flexibility but not inflating. However, in consideration of operability of the operator, the fluid storage portion 73 is preferably configured as a balloon type whose outer shape is inflatable or expandable by an amount of fluid to be stored among the illustrated configurations. This is because in a case where the fluid storage portion 73 is an inflatable balloon type, the outer shape is inflated by the amount of fluid to be stored, so that more gas can be stored in a smaller space than a tube type. The fluid storage portion 73 is an inflatable balloon type, and thus, a size of the injection member 50 can be reduced, so that it is possible to improve the operability without hindering operation of the operator. In addition, by the fluid storage portion 73 being configured to be inflatable, the amount of gas that can be degassed at one time (that is, a gas storage amount) can be increased, so that it is possible to reduce the number of times of degassing operation. In the fluid storage portion 73 using the inflatable material, a degree of inflation (volume increase amount) before and after inflation can be adjusted by appropriately setting a composition or thickness of the material to be used.

Figure 5A:
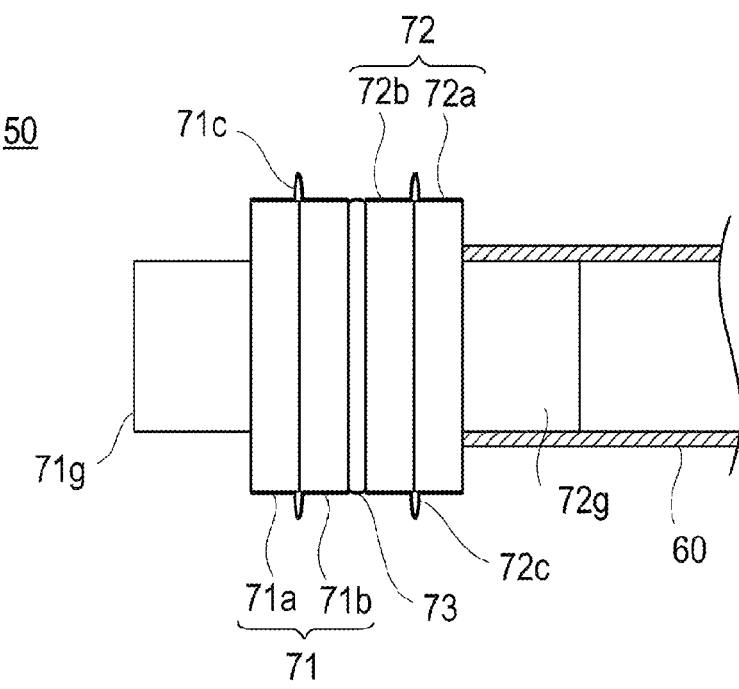
FIG. 5A is a view illustrating a state before the fluid storage portion is extended, which is one form of a fluid storage portion of the hemostatic device according to the present embodiment.
Figure 5B:
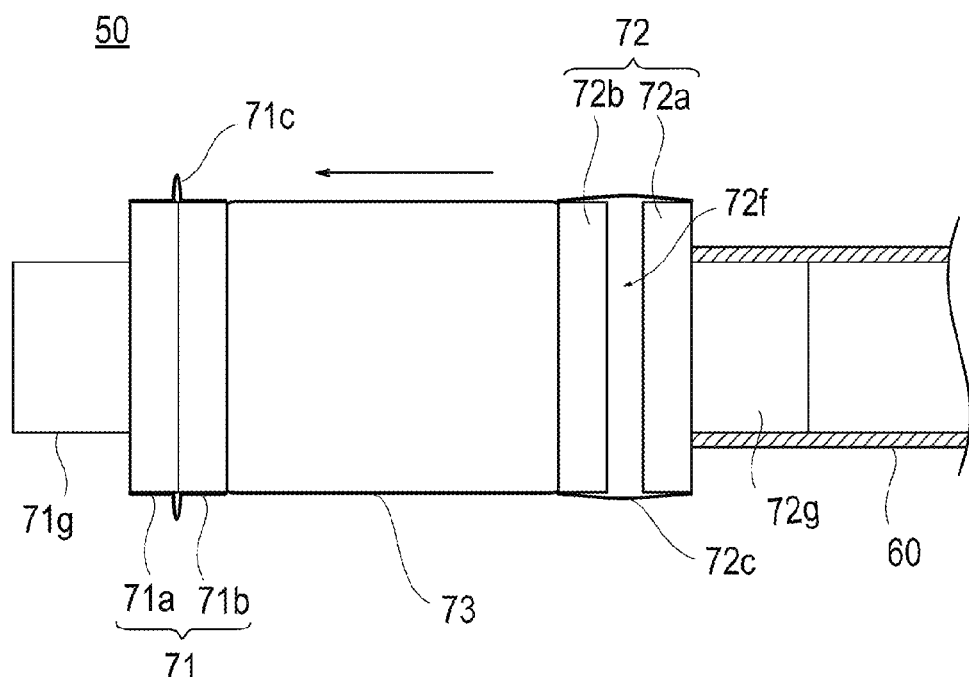
FIG. 5B is a view illustrating a state after the fluid storage portion is extended, which is one form of the fluid storage portion of the hemostatic device according to the present embodiment.

In addition, by the fluid storage portion 73 being made of an inflatable material having flexibility, a distance between the first valve member 71 and the second valve member 72 can be extended along the long axis (axial) direction of the injection member 50, and a storable volume can be increased. FIGS. 5A and 5B illustrate aspects before and after inflation of the fluid storage portion 73. As illustrated in FIG. 5A, the fluid storage portion 73 is in a contracted state between the first valve member 71 and the second valve member 72 in a state before inflation. As illustrated in FIG. 5B, if the first valve member 71 is moved in the direction of separating from the second valve member 72 by the operator, the fluid storage portion 73 inflates by a predetermined length along the long axis (axial) direction of the injection member 50, and an interval between the first valve member 71 and the second valve member 72 increases. The fluid storage portion 73 is not limited to the configuration that contracts as illustrated in FIG. 5A in the state before inflation and may be configured to maintain a state in which the first valve member 71 and the second valve member 72 are separated from each other by a predetermined distance.

Figure 6A:
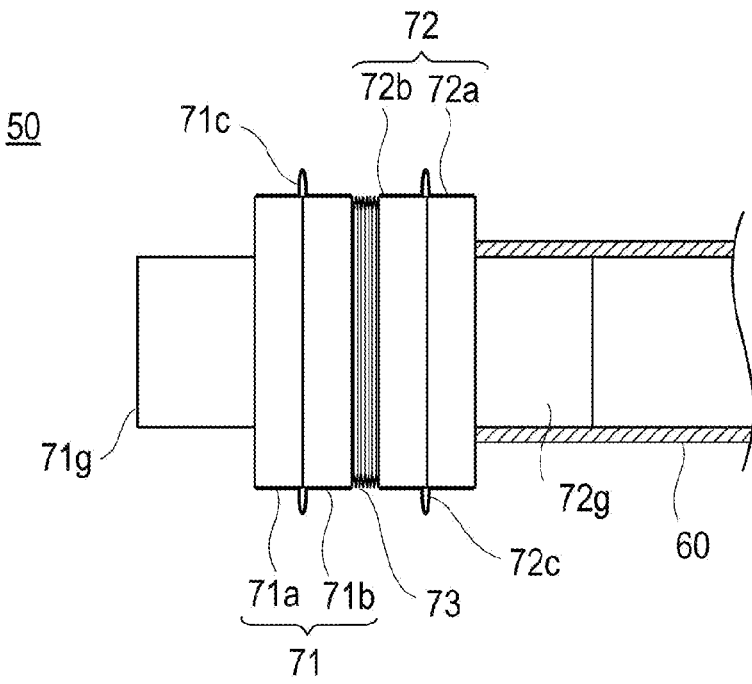
FIG. 6A is a view illustrating a state before the fluid storage portion is extended, which is another form of the fluid storage portion of the hemostatic device according to the present embodiment.
Figure 6B:
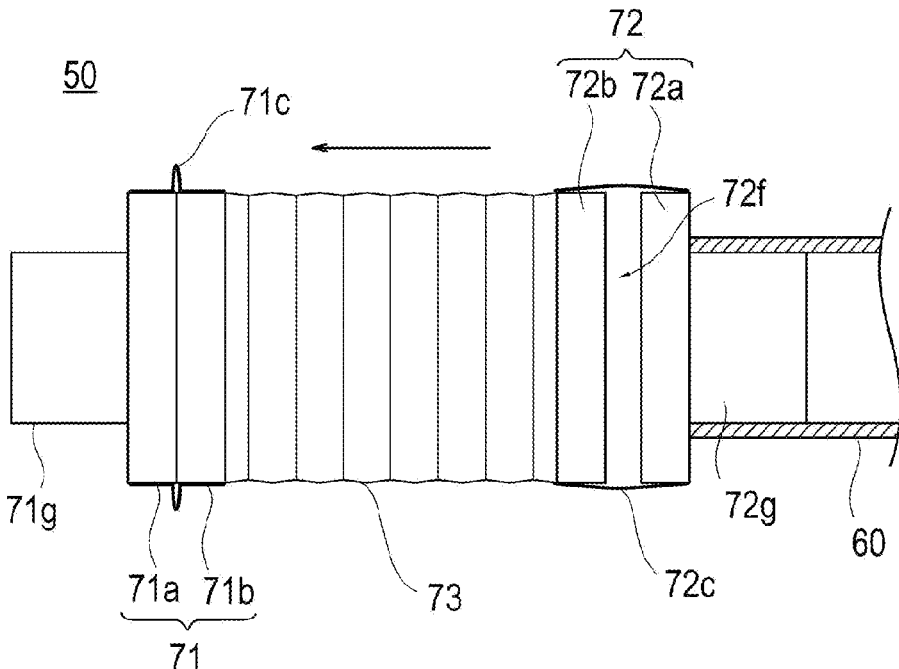
FIG. 6B is a view illustrating a state after the fluid storage portion is extended, which is another form of the fluid storage portion of the hemostatic device according to the present embodiment.

As illustrated in FIGS. 6A and 6B, the fluid storage portion 73 may adopt a bellows structure as another form for extending the distance between the first valve member 71 and the second valve member 72 along the long axis (axial) direction of the injection member 50 (extending the interval between the first valve member 71 and the second valve member 72). As illustrated in FIG. 6A, the fluid storage portion 73 is in a folded state between the first valve member 71 and the second valve member 72 in a state before inflation. As illustrated in FIG. 6B, if the first valve member 71 moves in a direction away from the second valve member 72 by the operator, the folded portion of the fluid storage portion 73 is developed and extends by a predetermined length along the axial direction of the injection member 50.

As illustrated in FIGS. 5A, 5B, 6A and 6B, the fluid storage portion 73 has a configuration capable of extending the interval (increasing the distance) between the first valve member 71 and the second valve member 72 to increase the volume that can be stored in the fluid storage portion 73. The hemostatic device 100 is generally degassed by a prescribed amount for each of a predetermined period according to a decompression protocol, but as the degassing operation is continued, the internal pressure in the inflatable member 30 gradually decreases, and a prescribed amount of gas may not flow. The fluid storage portion 73 has a configuration capable of extending or increasing the distance between the first valve member 71 and the second valve member 72 as described above, and thus, even if the flow amount (degassing amount) of the inflatable member 30 decreases, the distance between the first valve member 71 and the second valve member 72 can be extended or increased to generate a negative pressure in the fluid storage portion 73. As a result, the hemostatic device 100 can forcibly degas (suck) the inflatable member 30 by a predetermined amount of gas, so that the degassing operation according to the decompression protocol can be performed. In addition, the fluid storage portion 73 has the configuration illustrated in FIGS. 5A, 5B, 6A and 6B, and thus, the fluid storage portion 73 can be easily inflated until the interval between the first valve member 71 and the second valve member 72 reaches a predetermined length.

Thus, the fluid storage portion 73 also has a function of increasing the volume that can be stored in the fluid storage portion 73. As a result, in the fluid storage portion 73, the amount of gas that can be degassed at a time can be adjusted according to the interval (separation distance) between the first valve member 71 and the second valve member 72. Thus, by the operator adjusting the degassing amount to be stored in the fluid storage portion 73 and increasing the degassing amount to be larger than the prescribed degassing amount according to the decompression protocol to perform degassing, the number of times of degassing operation can be reduced.

The fluid storage portion 73 can be appropriately combined with the configurations illustrated in FIGS. 5A, 5B, 6A and 6B. In other words, the fluid storage portion 73 may have a bellows structure made of an inflatable material having flexibility.

The first valve member 71 includes a first securing and holding member 81 that maintains a state in which the first valve body 71a and the second valve body 71b are in close contact with each other. The second valve member 72 includes a second securing and holding member 82 that maintains a state in which the third valve body 72a and the fourth valve body 72b are in close contact with each other.

Figure 7A:
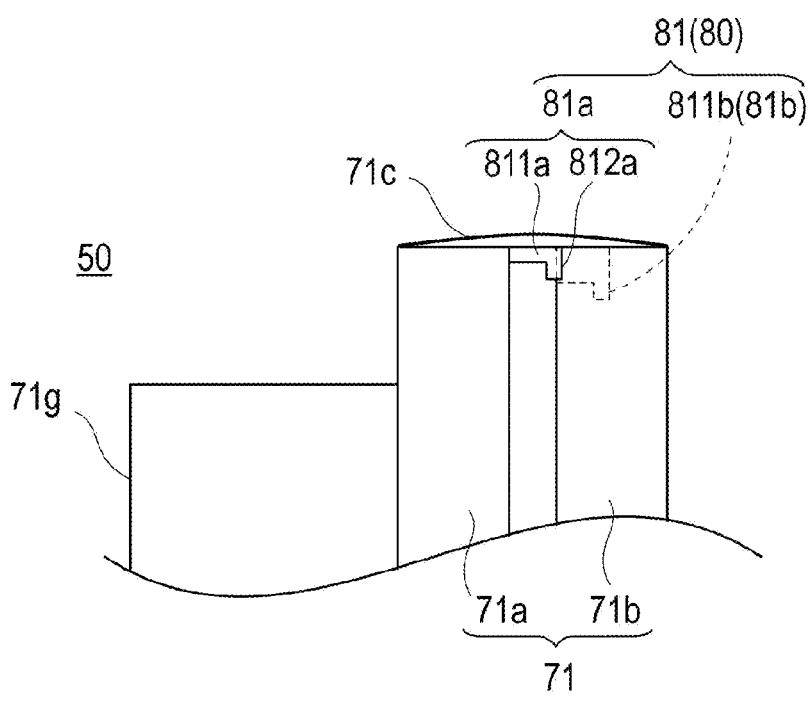
FIG. 7A is a view illustrating a state before engagement of a first securing and holding member of the hemostatic device according to the present embodiment.
Figure 7B:
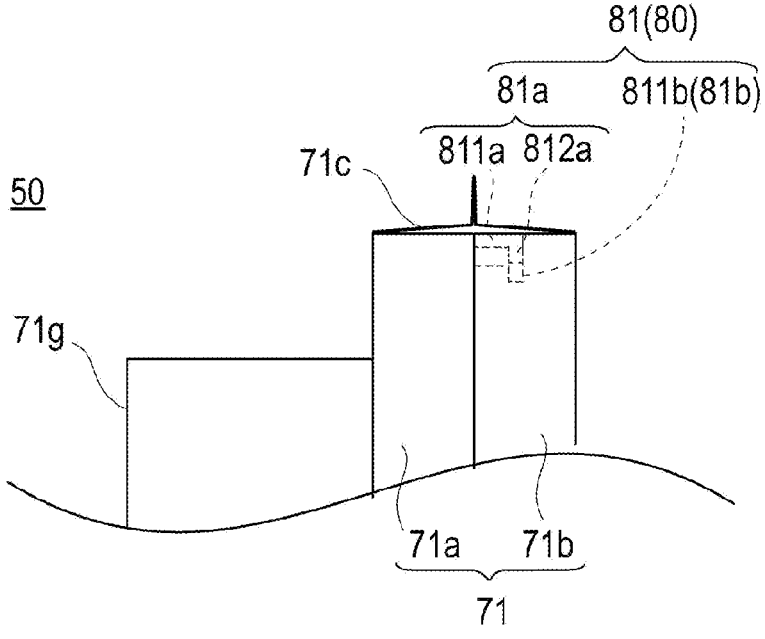
FIG. 7B is a view illustrating a state in the middle of engagement of the first securing and holding member of the hemostatic device according to the present embodiment.
Figure 7C:
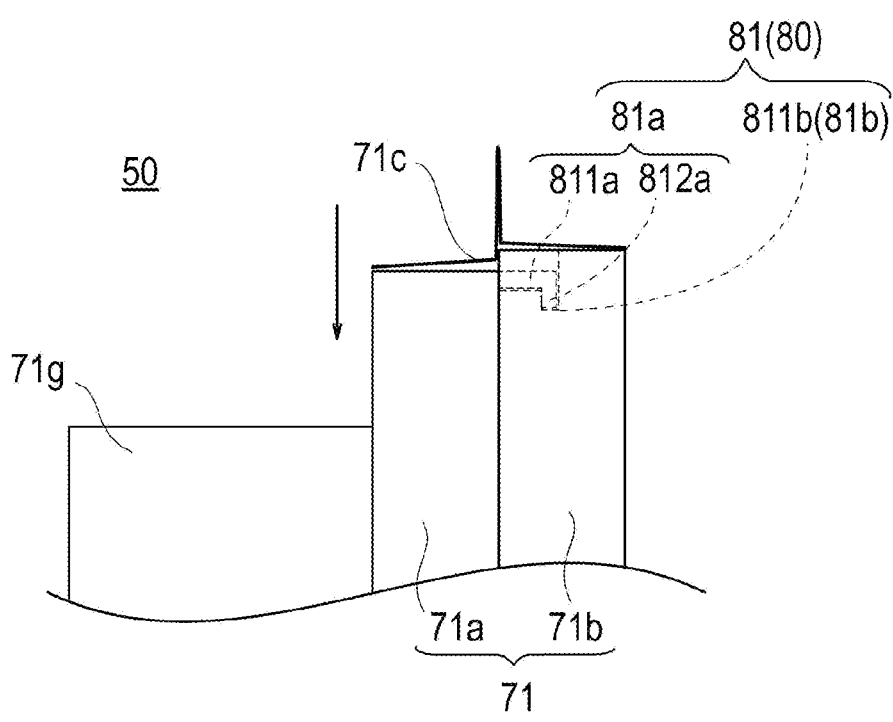
FIG. 7C is a view illustrating a state after engagement of the first securing and holding member of the hemostatic device according to the present embodiment.

The first securing and holding member 81 holds the first valve body 71a and the second valve body 71b in a state of being in close contact with each other. As illustrated in FIGS. 7A to 7C, the first securing and holding member 81 includes a first engagement portion 81a provided at the outer peripheral end portion on the distal side of the first valve body 71a and a second engagement portion 81b provided at the outer peripheral end portion on the proximal side of the second valve body 71b.

As an example, the first engagement portion 81a includes a base portion 811a protruding from an outer peripheral end portion on the distal side of the first valve body 71a toward the second valve body 71b, and a claw portion 812a formed in a hook shape by bending the distal side of the base portion 811a in a direction orthogonal to the long axis (axial) direction of the injection member 50. As an example, the second engagement portion 81b is constituted by a recess portion 811b provided at the outer peripheral end portion on the proximal side of the second valve body 71b and engaged with the claw portion 812a.

As illustrated in FIG. 7A, the first valve body 71a and the second valve body 71b are separated from each other as illustrated in the drawing, for example, when the gas stored in the fluid storage portion 73 is degassed to the outside. When the first valve body 71a and the second valve body 71b are brought into close contact with each other again after the gas is degassed, the first valve body 71a is brought close to the second valve body 71b as illustrated in FIG. 7B. In this event, the end surface of the first valve body 71a and the end surface of the second valve body 71b are in close contact with each other, but the first engagement portion 81a and the second engagement portion 81b are not yet engaged with each other. Then, as illustrated in FIG. 7C, the first valve body 71*a* (or the second valve body 71*b*) is relatively moved in a direction orthogonal to the long axis (axial) direction of the second valve body 71*b* (or the first valve body 71*a*) and the injection member 50 to engage the first engagement portion 81*a* and the second engagement portion 81*b*. As illustrated in FIG. 7C, when the first engagement portion 81*a* and the second engagement portion 81*b* are engaged with each other, the claw portion 812*a* is in a state of being fitted in the recess portion 811*b*. As a result, the first valve body 71*a* and the second valve body 71*b* are kept in close contact with each other.

The first securing and holding member 81 only needs to be able to hold (secure) the first valve body 71*a* and the second valve body 71*b* in a state of being in close contact with each other, and thus, structures of the first engagement portion 81*a* and the second engagement portion 81*b* may be interchanged. In addition, the first valve body 71*a* and the second valve body 71*b* may be arranged such that, in a state before the first engagement portion 81*a* and the second engagement portion 81*b* are engaged, part of the first engagement portion 81*a* abuts on part of the second engagement portion 81*b* as illustrated in FIG. 7A, but part of the first engagement portion 81*a* does not have to abut on part of the second engagement portion 81*b*.

Figure 8A:
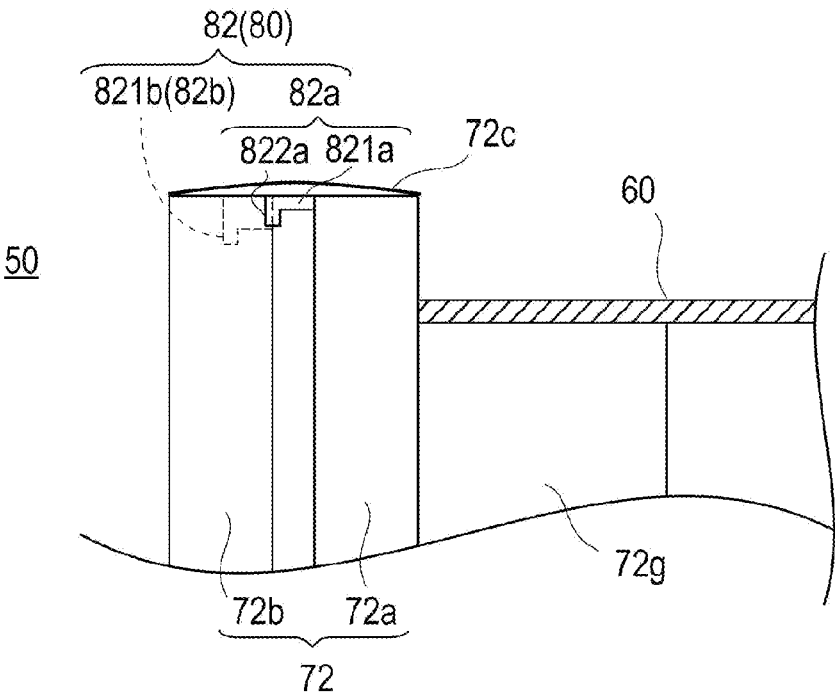
FIG. 8A is a view illustrating a state before engagement of a second securing and holding member of the hemostatic device according to the present embodiment.
Figure 8B:
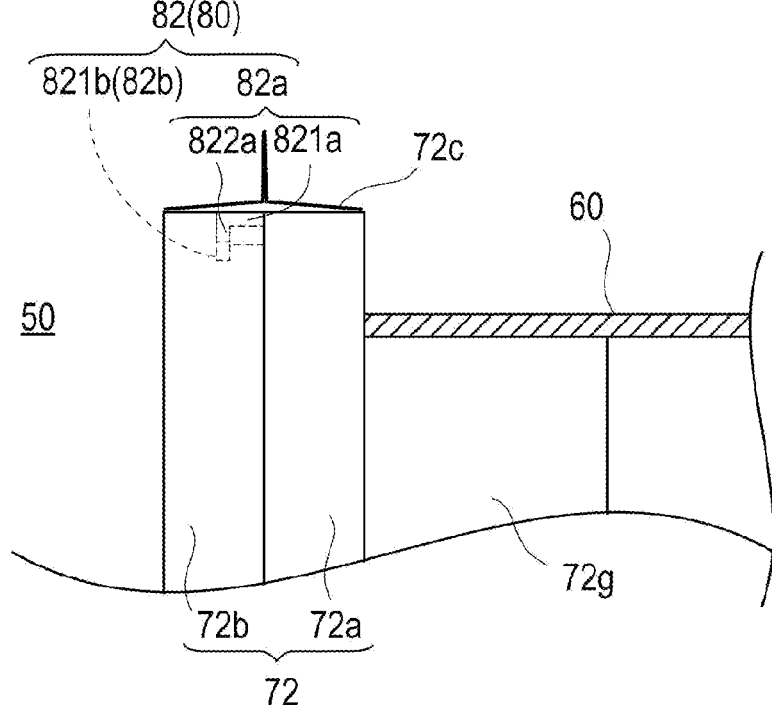
FIG. 8B is a view illustrating a state in the middle of engagement of the second securing and holding member of the hemostatic device according to the present embodiment.
Figure 8C:
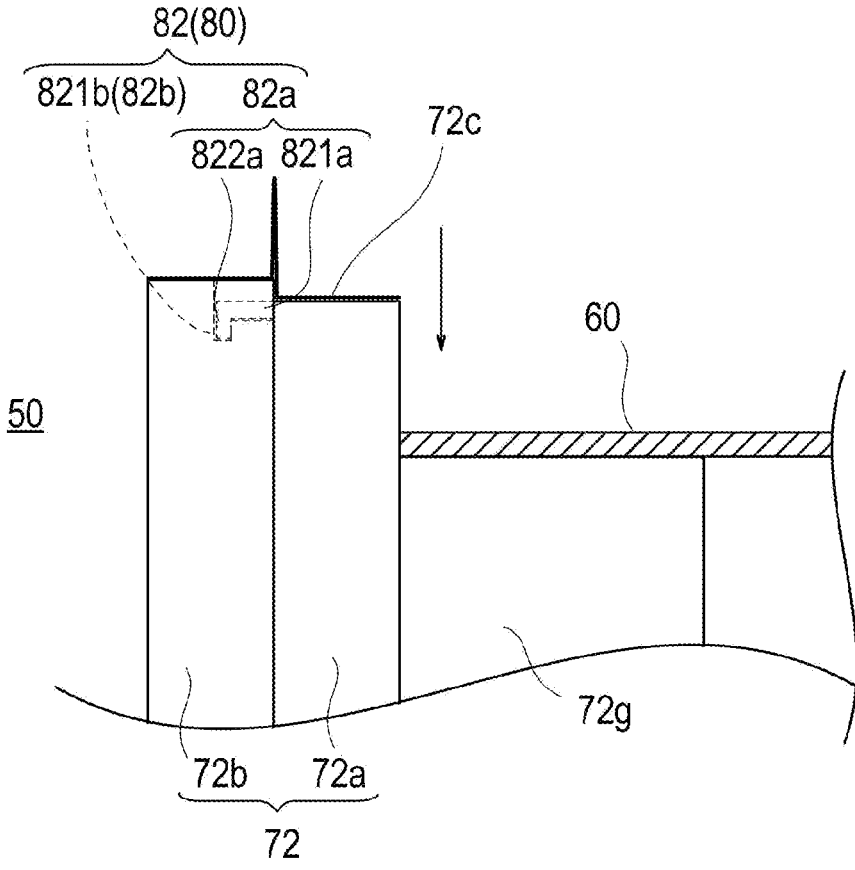
FIG. 8C is a view illustrating a state after engagement of the second securing and holding member of the hemostatic device according to the present embodiment.

The second securing and holding member 82 holds the third valve body 72*a* and the fourth valve body 72*b* in a state of being in close contact with each other. As illustrated in FIGS. 8A to 8C, the second securing and holding member 82 includes a third engagement portion 82*a* provided at the outer peripheral end portion on the proximal side of the third valve body 72*a* and a fourth engagement portion 82*b* provided at the outer peripheral end portion on the distal side of the fourth valve body 72*b*.

As an example, the third engagement portion 82*a* is constituted by a base portion 821*a* protruding toward the fourth valve body 72*b* from the outer peripheral end portion on the proximal side of the third valve body 72*a*, and a claw portion 822*a* formed in a hook shape by bending a distal side of the base portion 821*a* in a direction orthogonal to the long axis (axial) direction of the injection member 50. As an example, the fourth engagement portion 82*b* is constituted by a recess portion 821*b* provided at the outer peripheral end portion on the distal side of the fourth valve body 72*b* and engaged with the claw portion 822*a*.

As illustrated in FIG. 8A, for example, in a case where the gas in the inflatable member 30 is degassed, the third valve body 72*a* and the fourth valve body 72*b* are separated from each other as illustrated in the drawing. When the third valve body 72*a* and the fourth valve body 72*b* are brought into close contact with each other again after a predetermined amount of gas flows in the fluid storage portion 73, the third valve body 72*a* is brought close to the fourth valve body 72*b* as illustrated in FIG. 8B. In this event, the end surface of the third valve body 72*a* and the end surface of the fourth valve body 72*b* are in close contact with each other, but the third engagement portion 82*a* and the fourth engagement portion 82*b* are not yet engaged with each other. Then, as illustrated in FIG. 8C, the third valve body 72*a* (or the fourth valve body 72*b*) is relatively moved in a direction orthogonal to the long axis (axial) direction of the fourth valve body 72*b* (or the third valve body 72*a*) and the injection member 50 to engage the third engagement portion 82*a* and the fourth engagement portion 82*b*. As illustrated in FIG. 8C, when the third engagement portion 82*a* and the fourth engagement portion 82*b* are engaged with each other, the claw portion 822*a* is in a state of being fitted in the recess portion 821*b*.

As a result, the third valve body 72*a* and the fourth valve body 72*b* are kept in close contact with each other.

The second securing and holding member 82 only needs to be able to hold (secure) the third valve body 72*a* and the fourth valve body 72*b* in a state of being in close contact with each other, and thus, structures of the third engagement portion 82*a* and the fourth engagement portion 82*b* may be interchanged. In addition, the third valve body 72*a* and the fourth valve body 72*b* may be arranged such that, in a state before the third engagement portion 82*a* and the fourth engagement portion 82*b* are engaged, part of the third engagement portion 82*a* abuts on part of the fourth engagement portion 82*b* as illustrated in FIG. 8A, but part of the third engagement portion 82*a* does not have to abut on part of the fourth engagement portion 82*b*.

As described above, the first securing and holding member 81 holds the first valve body 71*a* and the second valve body 71*b* in a state of being in close contact with each other and holds the closed state of the first valve member 71 so as to block flow of gas. In addition, the second securing and holding member 82 holds the third valve body 72*a* and the fourth valve body 72*b* in a state of being in close contact with each other and holds the closed state of the second valve member 72 so as to block flow of gas.

The hemostatic device 100 includes the first securing and holding member 81 that holds the first valve member 71 in the closed state and the second securing and holding member 82 that holds the second valve member 72 in the closed state. Thus, in the hemostatic device 100, when the close contact state of the first valve body 71*a* and the second valve body 71*b* (the third valve body 72*a* and the fourth valve body 72*b*) is maintained, it is not necessary for the operator to maintain the close contact state of the first valve body 71*a* and the second valve body 71*b* (the third valve body 72*a* and the fourth valve body 72*b*) by hand (manually) or maintain the close contact state of the first valve body 71*a* and the second valve body 71*b* (the third valve body 72*a* and the fourth valve body 72*b*) by a separate body such as a clip. Thus, the hemostatic device 100 can reliably maintain the closed states of the first valve member 71 and the second valve member 72 with a simple structure, and even if the hemostatic device 100 comes into contact with another surrounding member (such as a desk, a bed and an indoor wall), the closed states of the first valve member 71 and the second valve member 72 are not released by action of the first securing and holding member 81 and the second securing and holding member 82. Thus, in the hemostatic device 100, unintended degassing operation, or the like, does not occur, and a compressive force on the puncture site by the inflatable member 30 can be appropriately maintained.

<Operation>

Next, usage examples of the hemostatic device 100 will be described with reference to FIGS. 9 to 13C. In the usage examples described below, the exemplary order is merely presented, and the presented order may be appropriately changed as long as the operation is not hindered.

As illustrated in FIG. 9, the hemostatic device 100 described below is used in a state where the band body 10 is wound around the wrist W and worn. In addition, in the worn state illustrated in FIG. 9, the hemostatic device 100 performs "injection operation" (see FIGS. 10A to 10F), "degassing operation" (see FIGS. 11A to 11E), "reinjection operation" (see FIGS. 12A to 12C), and "forced degassing operation" (see FIGS. 13A to 13C) as appropriate.

<Injection Operation>

The injection operation is operation for injecting a predetermined amount of gas into the inflatable member 30.

During the injection operation, the hemostatic device 100 is operated according to the procedure illustrated in FIGS. 10A to 10F as an example.

Figure 10A:
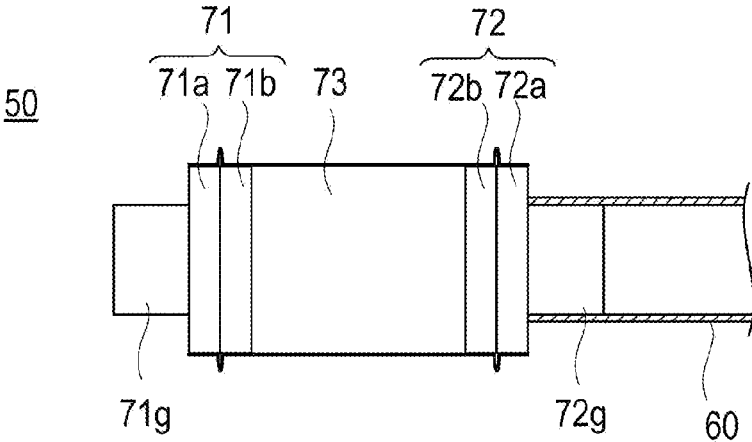
FIG. 10A is a view illustrating procedure of injection operation of the hemostatic device according to the present embodiment, and is a view in a state where a first valve member and a second valve member are closed.

As illustrated in FIG. 10A, in the hemostatic device 100, the first valve member 71 and the second valve member 72 are closed before the injection operation.

Figure 10B:
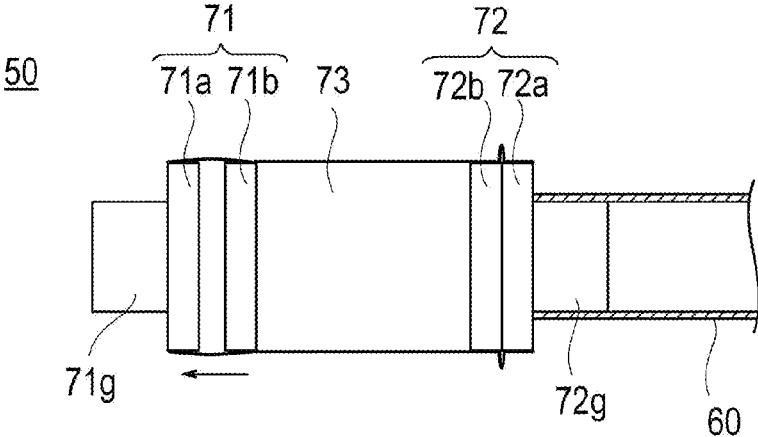
FIG. 10B is a view illustrating procedure of the injection operation of the hemostatic device according to the present embodiment, and is a view in a state where the first valve member is in an open state.
Figure 10C:
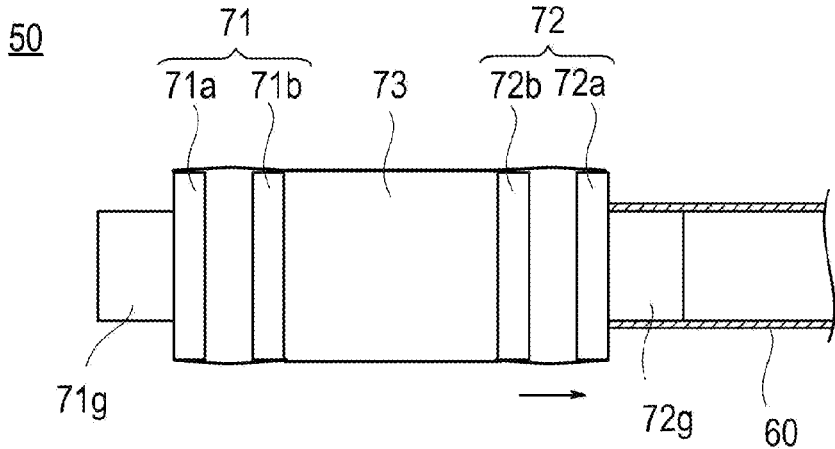
FIG. 10C is a view illustrating procedure of the injection operation of the hemostatic device according to the present embodiment, and is a view in a state where the second valve member is in an open state.

As illustrated in FIG. 10B, the operator first releases the close contact state between the first valve body 71*a* and the second valve body 71*b* of the first valve member 71 to separate them from each other. As a result, the first valve member 71 is in an open state, and gas can flow. Next, as illustrated in FIG. 10C, the operator releases the close contact state between the third valve body 72*a* and the fourth valve body 72*b* of the second valve member 72 to separate them from each other. As a result, the second valve member 72 is in an open state, and gas can flow.

Figure 10D:
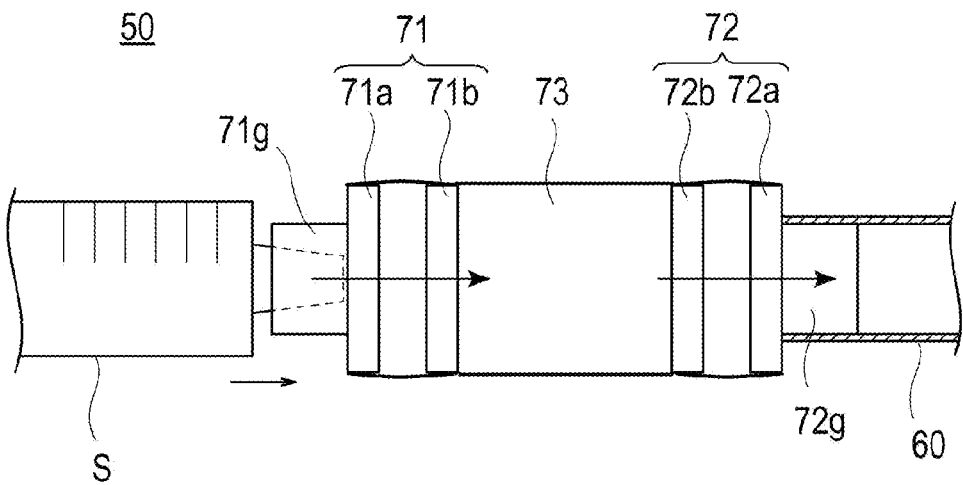
FIG. 10D is a view illustrating procedure of the injection operation of the hemostatic device according to the present embodiment, and is a view illustrating a state during fluid injection by an injection instrument (syringe).

As illustrated in FIG. 10D, the operator attaches the syringe S to the first protruding portion 71*g* functioning as the connector portion and operates the pusher of the syringe S to inject an amount of gas corresponding to the volume of the inflatable member 30. The injected gas flows to the inflatable member 30 through the first valve member 71, the fluid storage portion 73, the second valve member 72, and the tube 60 in this order.

Figure 10E:
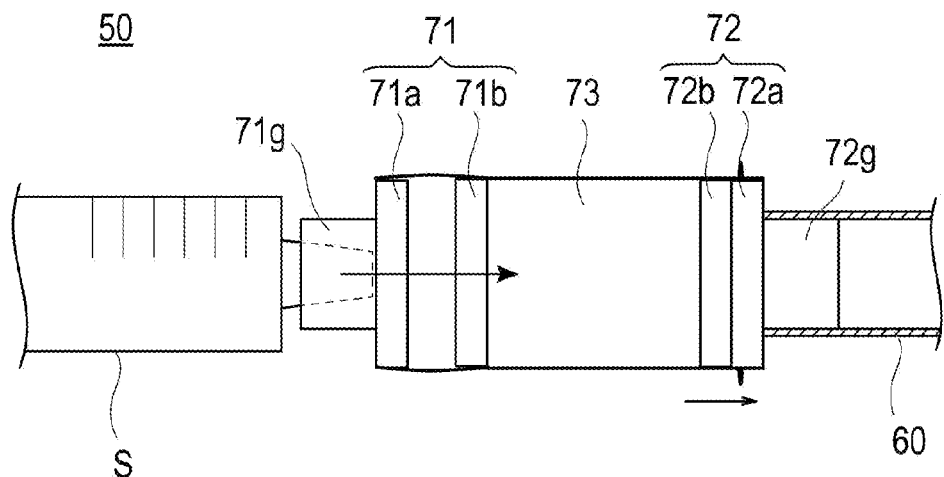
FIG. 10E is a view illustrating procedure of the injection operation of the hemostatic device according to the present embodiment, and is a view in a state where the second valve member is closed.

When the injection of the gas into the inflatable member 30 is completed, as illustrated in FIG. 10E, the operator brings the third valve body 72*a* and the fourth valve body 72*b* into close contact with each other to close the second valve member 72. As a result, the second valve member 72 is put into the closed state, and thus, the gas injected into the inflatable member 30 does not flow out to the outside through the injection member 50.

Figure 10F:
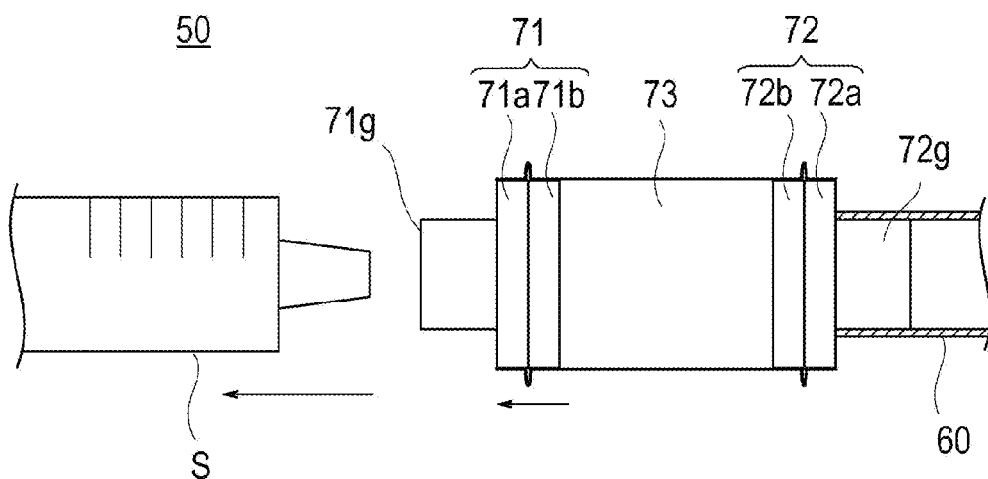
FIG. 10F is a view illustrating procedure of the injection operation of the hemostatic device according to the present embodiment, and is a view in a state where the first valve member is closed.

Thereafter, as illustrated in FIG. 10F, the operator brings the first valve body 71*a* and the second valve body 71*b* into close contact with each other to bring the first valve member 71 into a closed state and then disengages the syringe S from the first protruding portion 71*g* to end the injection operation. As a result, the puncture site of the patient is compressed by the inflatable member 30, and the hemostatic treatment is started.

In the hemostatic device 100, the first valve member 71 and the second valve member 72 may be in an open state before the band body 10 is worn on the wrist W. In this case, after the hemostatic device 100 is worn on the patient, as illustrated in FIG. 9, the operator can omit operation of opening the first valve member 71 and the second valve member 72, and as illustrated in FIG. 10D, the operator can attach the syringe S to the first protruding portion 71*g* functioning as the connector portion and operate the pusher of the syringe S to inject the gas in an amount corresponding to the volume of the inflatable member 30.

<Degassing Operation (Fluid Discharge Operation)>

The degassing operation is an operation for degassing a predetermined amount of gas from the inflatable member 30 for each of a predetermined period according to a predetermined decompression protocol. During the degassing operation, the hemostatic device 100 is operated according to the procedure illustrated in FIGS. 11A to 11E as an example.

Figure 11A:
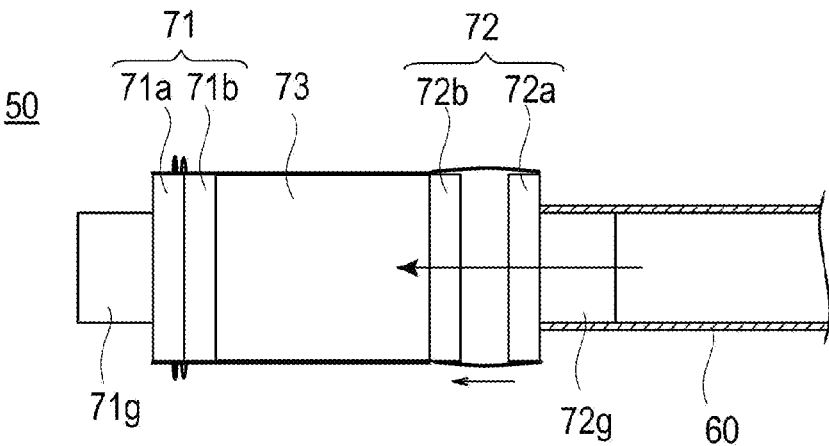
FIG. 11A is a view illustrating procedure of degassing operation of the hemostatic device according to the present embodiment, and is a view in a state where the second valve member is in an open state.

As illustrated in FIG. 11A, the operator separates the third valve body 72*a* and the fourth valve body 72*b* to bring the second valve member 72 into an open state. As a result, the gas stored in the inflatable member 30 flows to the fluid storage portion 73 due to a pressure difference between the internal pressure in the inflatable member 30 and the internal pressure in the fluid storage portion 73.

Figure 11B:
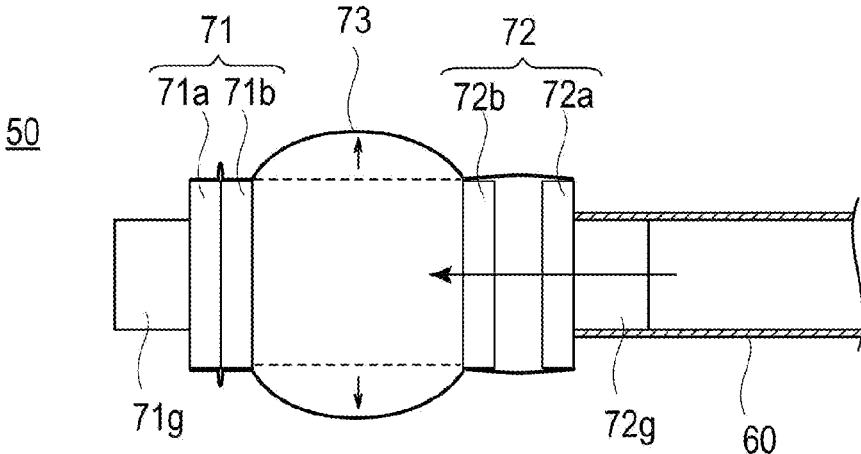
FIG. 11B is a view illustrating procedure of the degassing operation of the hemostatic device according to the present embodiment, and is a view illustrating a state where a fluid flows in the fluid storage portion.
Figure 11C:
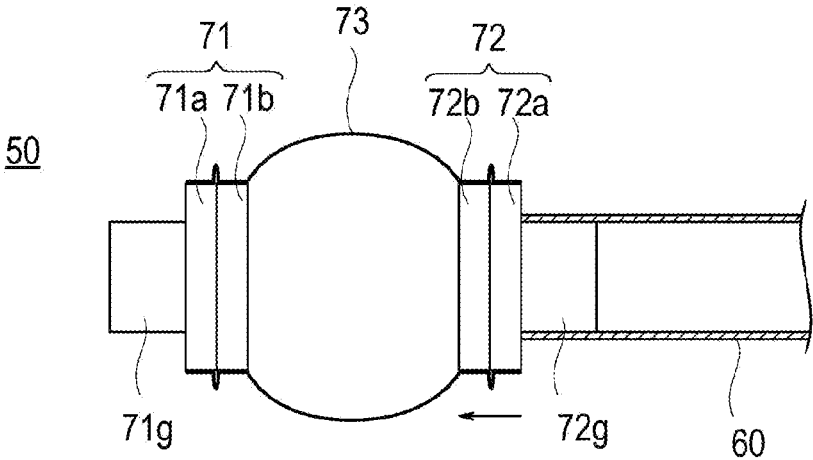
FIG. 11C is a view illustrating procedure of the degassing operation of the hemostatic device according to the present embodiment, and is a view in a state where the second valve member is closed.

As illustrated in FIG. 11B, the operator confirms that a predetermined amount of gas flows from the inflatable member 30 to the fluid storage portion 73, and the fluid storage portion 73 inflates and is filled with the gas. Thereafter, as illustrated in FIG. 11C, the third valve body 72*a* and the fourth valve body 72*b* are brought into close contact with each other to bring the second valve member 72 into a closed state. As a result, the flow of gas from the inflatable member 30 to the fluid storage portion 73 is blocked.

Figure 11D:
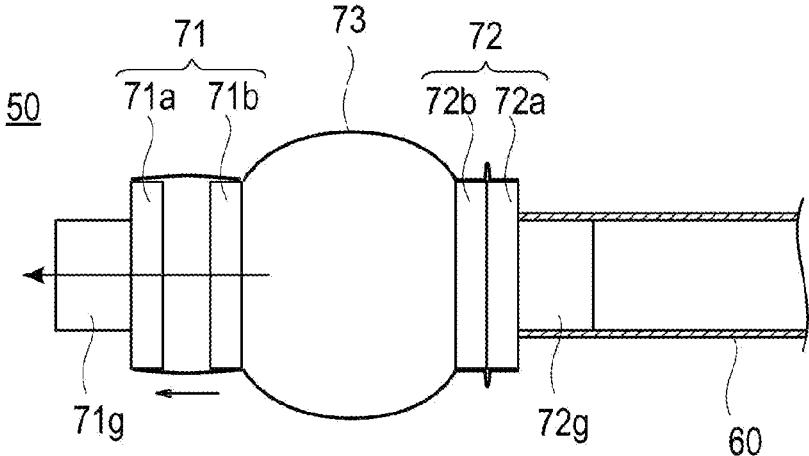
FIG. 11D is a view illustrating the procedure of the degassing operation of the hemostatic device according to the present embodiment, and is a view in a state where the first valve member is in an open state.
Figure 11E:
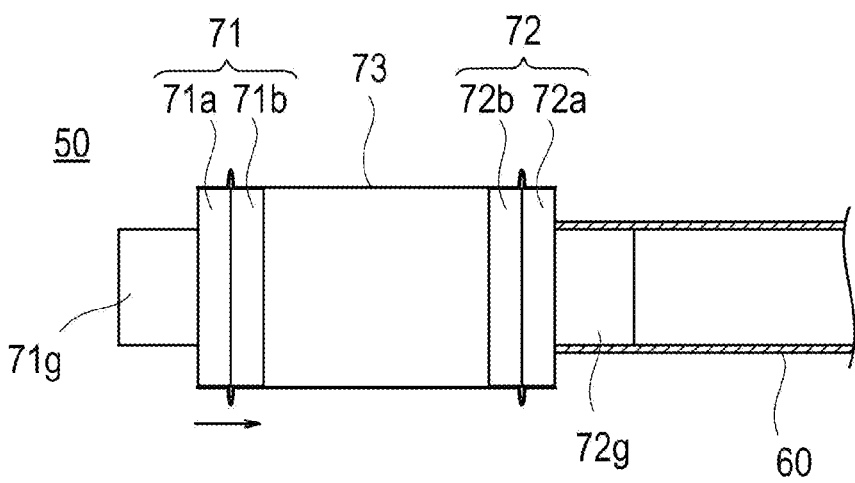
FIG. 11E is a view illustrating procedure of the degassing operation of the hemostatic device according to the present embodiment, and is a view illustrating a state where a fluid is discharged from the fluid storage portion.

Thereafter, as illustrated in FIG. 11D, the operator separates the first valve body 71*a* and the second valve body 71*b* to bring the first valve member 71 into an open state and degasses the gas stored in the fluid storage portion 73 to the outside to end the degassing operation. As illustrated in FIG. 11E, after the degassing operation is completed, the operator brings the first valve body 71*a* and the second valve body 71*b* into close contact with each other to bring the first valve member 71 into a closed state.

<Reinjection Operation>

The reinjection operation is an operation for returning the gas temporarily stored in the fluid storage portion 73 to the inflatable member 30 again in a case where it is determined that the amount of gas to be degassed from the inflatable member 30 is large on the basis of a hemostatic state of the puncture site. During the reinjection operation, the hemostatic device 100 is operated according to the procedure illustrated in FIGS. 12A to 12C as an example.

Figure 12A:
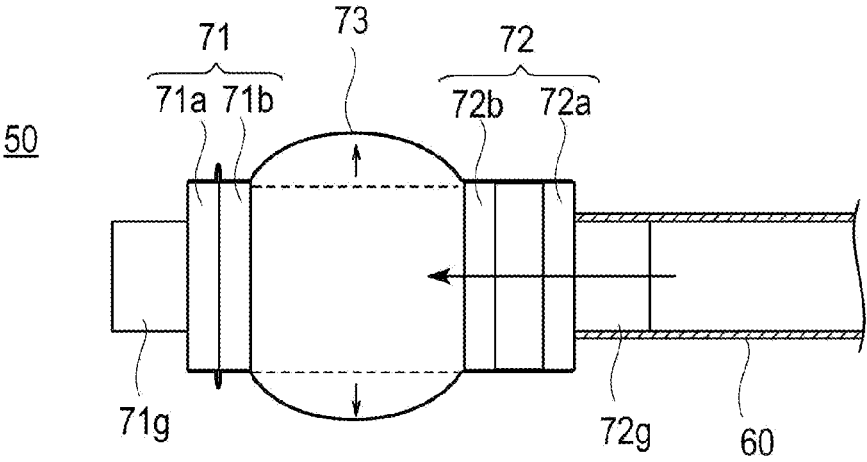
FIG. 12A is a view illustrating procedure of reinjection operation of the hemostatic device according to the present embodiment, and is a view in a state where the second valve member is in an open state.
Figure 12B:
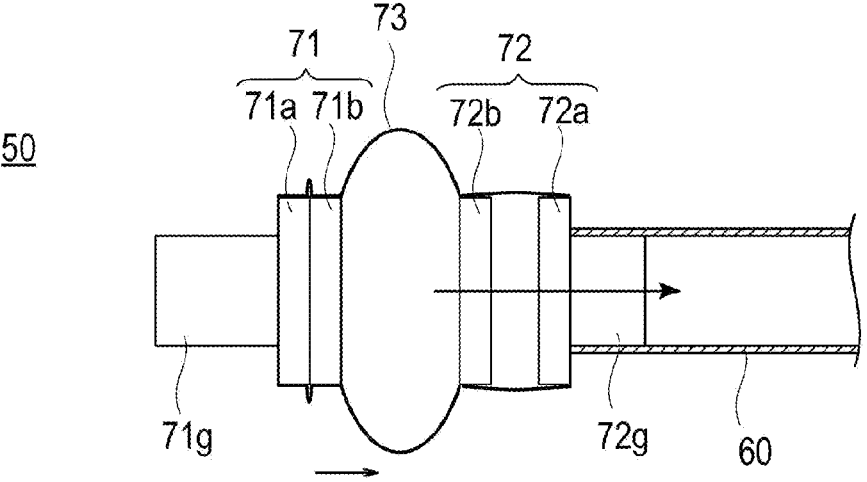
FIG. 12B is a view illustrating procedure of the reinjection operation of the hemostatic device according to the present embodiment, and is a view illustrating a state where the first valve member is brought close to the second valve member (state during the reinjection operation).

As illustrated in FIG. 12A, the operator separates the third valve body 72*a* and the fourth valve body 72*b* to bring the second valve member 72 into an open state and stores gas in the fluid storage portion 73. This processing is similar to the degassing operation illustrated in FIGS. 11A and 11B. In this event, in a case where the hemostatic state of the patient is not good and it is determined that it is necessary to inject the gas again, the operator brings the first valve member 71 close to the second valve member 72 and starts reinjection of the gas stored in the fluid storage portion 73 as illustrated in FIG. 12B.

Figure 12C:
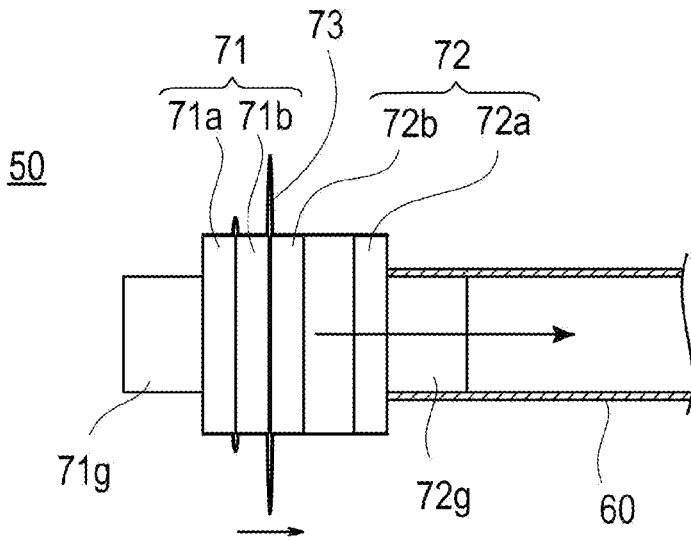
FIG. 12C is a view illustrating procedure of the reinjection operation of the hemostatic device according to the present embodiment, and is a view illustrating a state where a fluid is reinjected by bringing the first valve member close to the second valve member.

Thereafter, as illustrated in FIG. 12C, the operator brings the first valve member 71 closer to the second valve member 72 to inject the gas stored in the fluid storage portion 73 and then brings the third valve body 72*a* and the fourth valve body 72*b* into close contact with each other to bring the second valve member 72 into a closed state and ends the reinjection operation. As a result, the gas stored in the fluid storage portion 73 is injected again into the inflatable member 30, and the internal pressure (expansion degree) of the inflatable member 30 returns to the state before the reinjection operation.

<Forced Degassing Operation (Forced Discharge Operation of Fluid)>

The forced degassing operation is operation for forcibly degassing the gas in the inflatable member 30 in a case where it is determined that the amount of gas to be degassed from the inflatable member 30 is smaller than the prescribed amount. During the forced degassing operation, the hemostatic device 100 is operated according to the procedure illustrated in FIGS. 13A to 13C as an example.

Figure 13A:
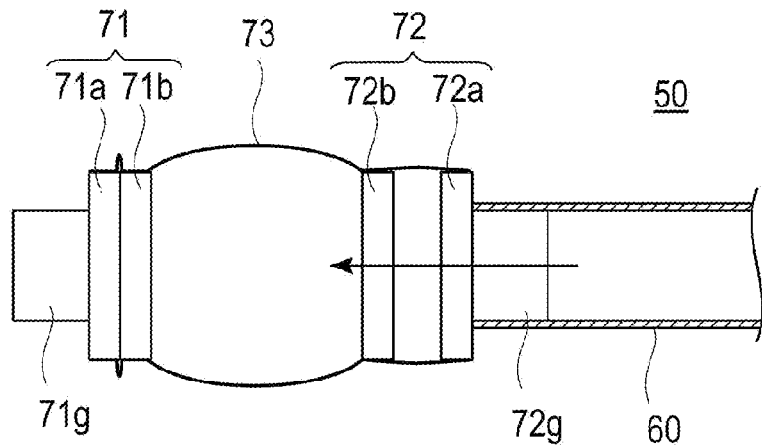
FIG. 13A is a view illustrating procedure of forced degassing operation of the hemostatic device according to the present embodiment, and is a view in a state where the second valve member is in an open state.
Figure 13B:
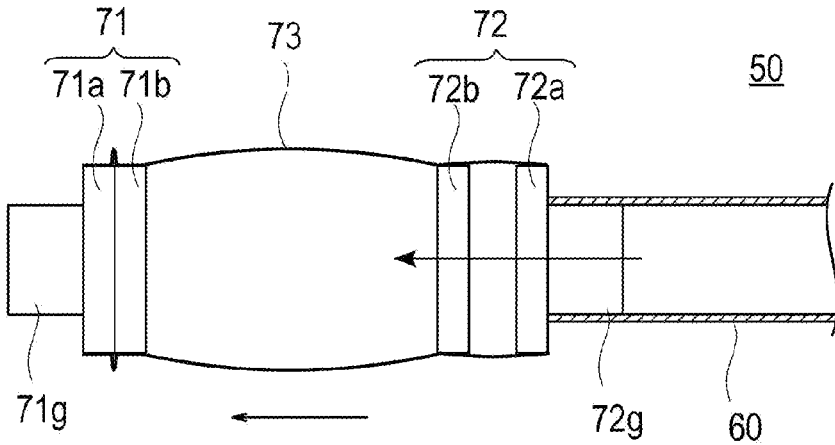
FIG. 13B is a view illustrating procedure of the forced degassing operation of the hemostatic device according to the present embodiment, and is a view illustrating a state where the first valve member is separated from the second valve member and a fluid is discharged from an inflatable member.

As illustrated in FIG. 13A, in the inflatable member 30, the internal pressure of the inflatable member 30 decreases by repeating the degassing operation, and the pressure difference between the internal pressure of the inflatable member 30 and the internal pressure of the fluid storage portion 73 decreases, so that the amount of gas flowing to the fluid storage portion 73 may decrease. In a case where the operator determines that the amount of flow from the inflatable member 30 has decreased to be smaller than the prescribed amount, as illustrated in FIG. 13B, the third valve body 72*a* and the fourth valve body 72*b* are separated from each other to bring the second valve member 72 into an open state, and in this state, the first valve member 71 is further separated from the second valve member 72 to extend the fluid storage portion 73 in the long axis (axial) direction. As a result, a negative pressure is generated inside the fluid storage portion 73, and a predetermined amount of gas can be forcibly removed from the inflatable member 30.

Figure 13C:
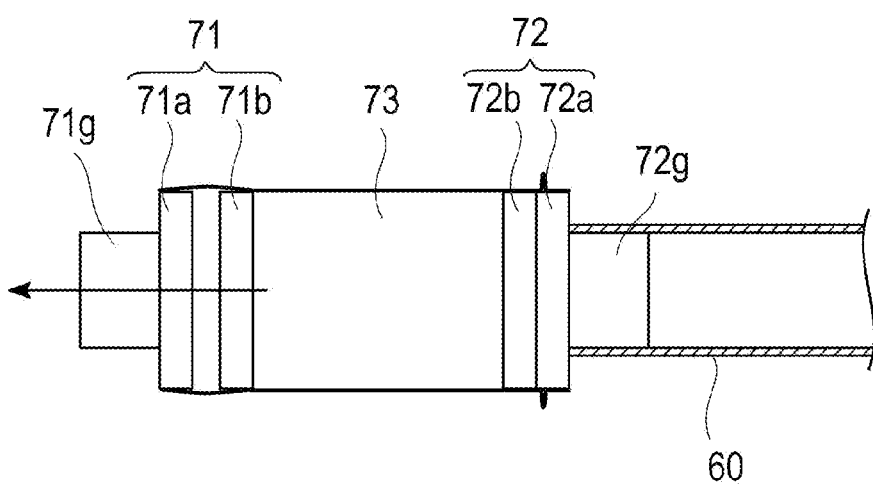
FIG. 13C is a view illustrating the procedure of the forced degassing operation of the hemostatic device according to the present embodiment, and is a view in a state where the second valve member is closed and the first valve member is in an open state.

Thereafter, as illustrated in FIG. 13C, the operator brings the third valve body 72*a* and the fourth valve body 72*b* into close contact with each other to bring the second valve member 72 into a closed state, then separates the first valve body 71*a* and the second valve body 71*b* to bring the first valve member 71 into an open state and degasses the gas stored in the fluid storage portion 73 to the outside to end the forced degassing operation.

MODIFICATIONS

Next, modifications of the hemostatic device 100 disclosed here will be described. In first to third modifications described below, constituent elements having the same functions as those in the above-described embodiment may be denoted by the same reference numerals and detailed description thereof may be omitted, and configurations, members, usage methods, and the like, that are not particularly mentioned may be similar to those in the above-described embodiment. Furthermore, the configuration of the present embodiment and the configurations of the first to the third modifications can be implemented in any combination without departing from the gist of the hemostatic device disclosed here.

The first to the third modifications described below all describe modifications of the securing and holding member 80 for maintaining the closed states of the first valve member 71 and the second valve member 72.

First Modification

Figure 14A:
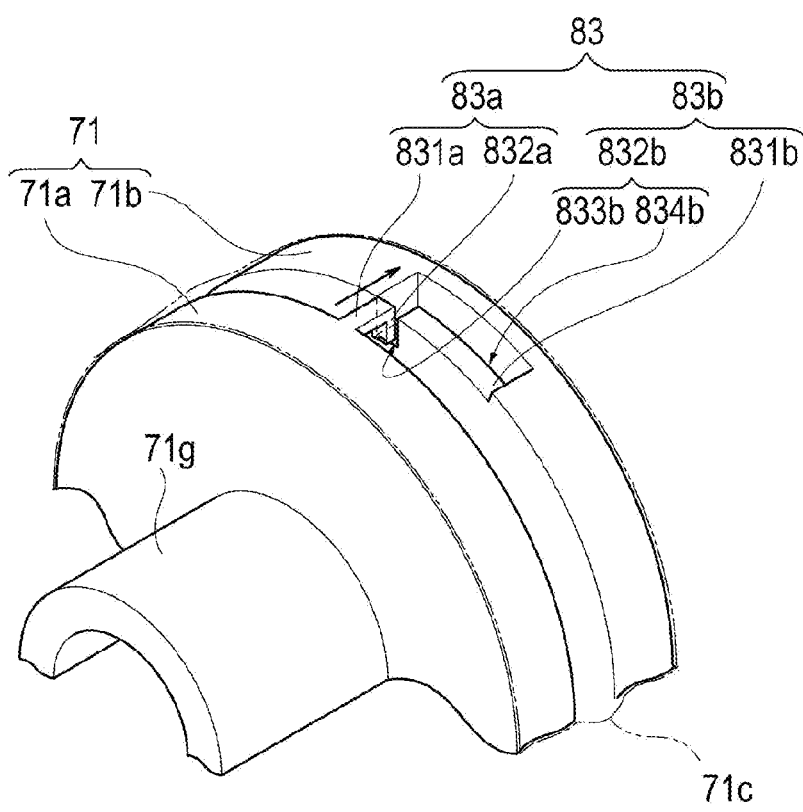
FIG. 14A is a view illustrating a state before engagement of the first securing and holding member of the hemostatic device according to the present embodiment.
Figure 14B:
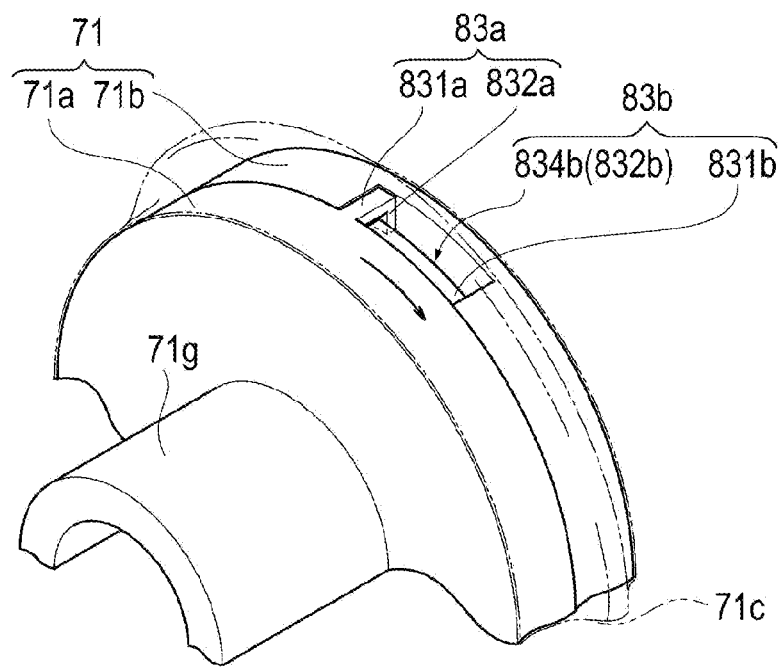
FIG. 14B is a view illustrating a state in the middle of engagement of a first securing and holding member of a hemostatic device according to a first modification.
Figure 15A:
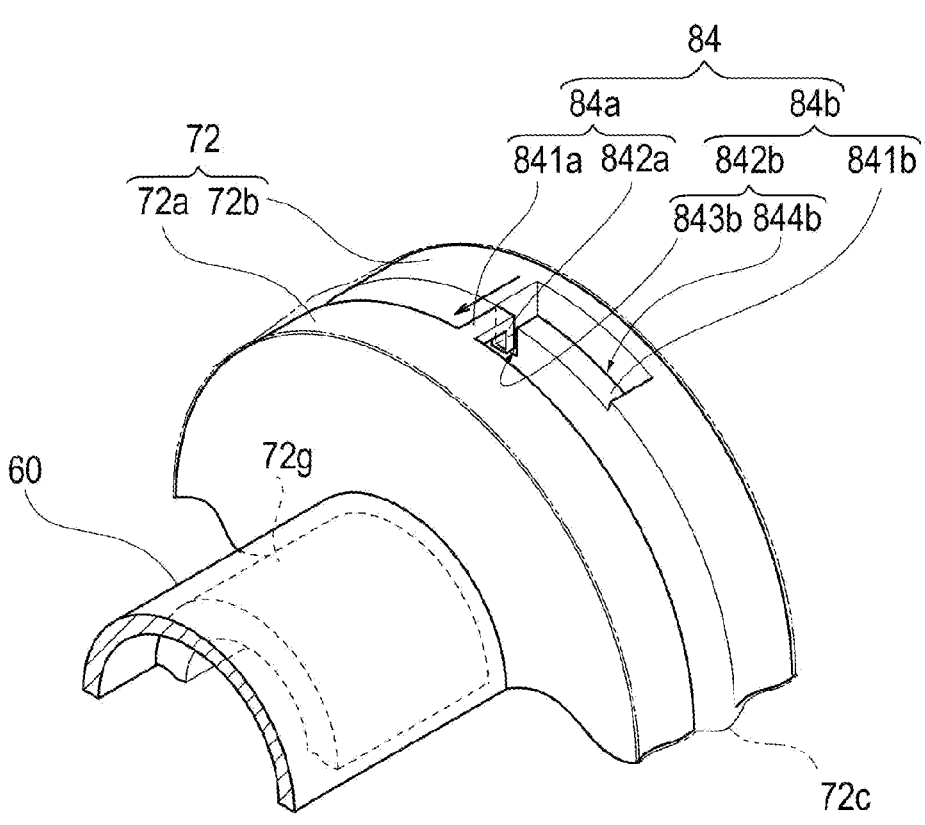
FIG. 15A is a view illustrating a state before engagement of a second securing and holding member of the hemostatic device according to the first modification.
Figure 15B:
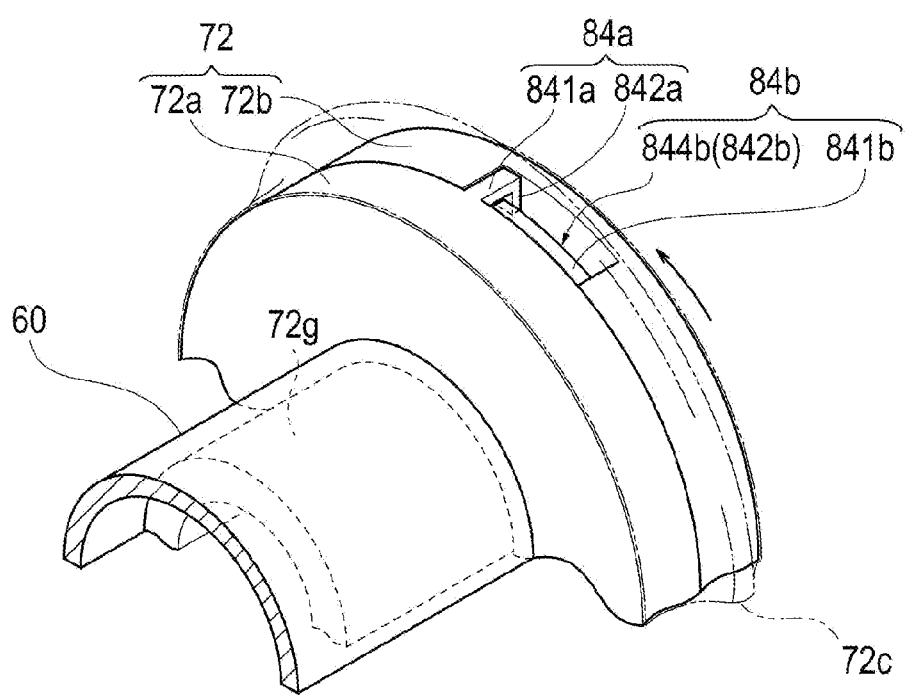
FIG. 15B is a view illustrating a state in the middle of engagement of the second securing and holding member of the hemostatic device according to the first modification.

The first modification of the hemostatic device 100 will be described with reference to FIGS. 14A, 14B, 15A and 15B. In the hemostatic device 100 of the first modification, a first securing and holding member 83 and a second securing and holding member 84 have different engagement forms from the first securing and holding member 81 and the second securing and holding member 82 in the above-described embodiment. FIGS. 14A and 14B illustrate the first securing and holding member 83 as a modification of the configuration of the first securing and holding member 81, and FIGS. 15A and 15B illustrate the second securing and holding member 84 as a modification of the second securing and holding member 82.

Figure 14C:
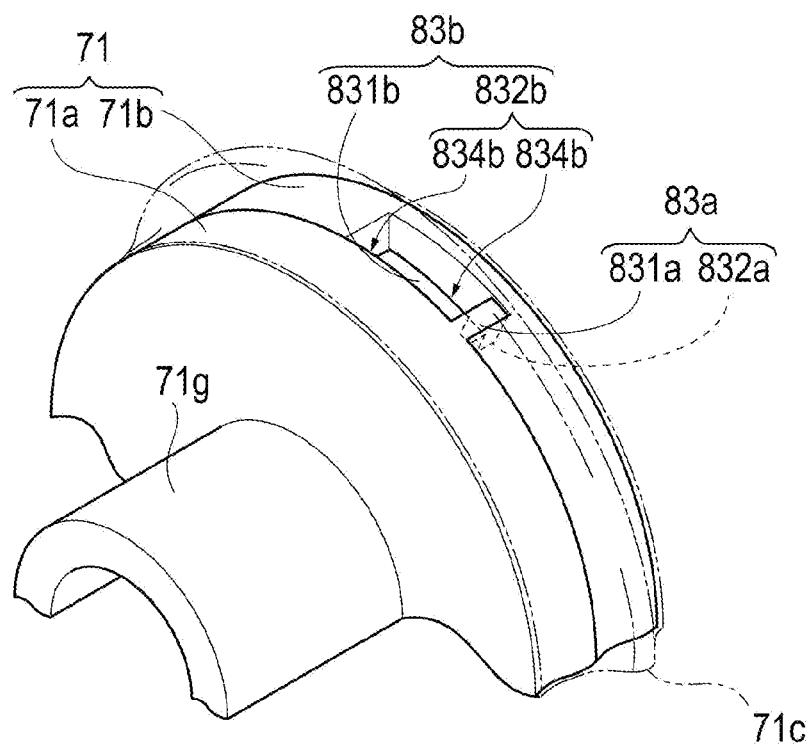
FIG. 14C is a view illustrating a state after engagement of the first securing and holding member of the hemostatic device according to the first modification.
Figure 15C:
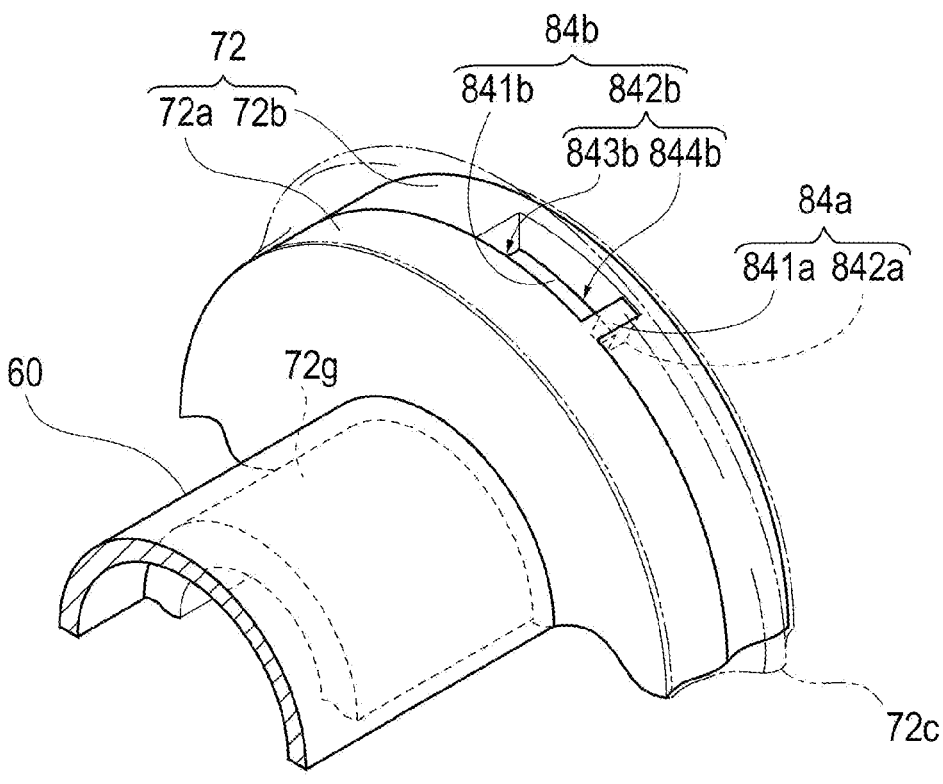
FIG. 15C is a view illustrating a state after engagement of the second securing and holding member of the hemostatic device according to the first modification.

In the hemostatic device 100 of the first modification, as illustrated in FIGS. 14A to 14C, the first valve member 71 includes the first securing and holding member 83 that maintains a state in which the first valve body 71*a* and the second valve body 71*b* are in close contact with each other. As illustrated in FIGS. 15A to 15C, the second valve member 72 includes the second securing and holding member 84 that maintains a state in which the third valve body 72*a* and the fourth valve body 72*b* are in close contact with each other.

The first securing and holding member 83 holds the first valve body 71*a* and the second valve body 71*b* in a state of being in close contact with each other. As illustrated in FIGS. 14A to 14C, the first securing and holding member 83 includes a first engagement portion 83*a* provided at the outer peripheral end portion on the distal side of the first valve body 71*a* and a second engagement portion 83*b* provided at the outer peripheral end portion on the proximal side of the second valve body 71*b*.

The first engagement portion 83*a* is engaged with the second engagement portion 83*b*. As an example, the first engagement portion 83*a* includes a base portion 831*a* protruding from an outer peripheral end portion on the distal side of the first valve body 71*a* toward the second valve body 71*b*, and a claw portion 832*a* formed in a hook shape by bending the distal side of the base portion 831*a* in a direction orthogonal to the long axis (axial) direction of the injection member 50.

The second engagement portion 83*b* is engaged with the first engagement portion 83*a*. As an example, the second engagement portion 83*b* is constituted by a recessed groove including a first groove portion 831*b* that is provided along the outer peripheral end portion on the proximal side of the second valve body 71*b* and engaged with the base portion 831*a* when engaged with the first engagement portion 83*a*, and a second groove portion 832*b* that is engaged with the claw portion 832*a* when engaged with the first engagement portion 83*a* with a groove depth deeper than the first groove portion 831*b*. The second groove portion 832*b* has an insertion portion 833*b* into which the claw portion 832*a* is to be inserted. In addition, the second groove portion 832*b* has a guide portion 834*b* that guides movement of the claw portion 832*a* when the first valve body 71*a* is relatively moved (rotational movement along the circumferential direction) with respect to the second valve body 71*b* in a state where the claw portion 832*a* is inserted into the insertion portion 833*b*. The insertion portion 833*b* extends in the thickness direction in the second valve body 71*b*, and the guide portion 834*b* extends from a terminal end portion (butt portion) of the insertion portion 833*b* along the outer peripheral direction of the second valve body 71*b* by a predetermined length.

In addition, the first valve body 71*a* and the second valve body 71*b* are preferably disposed such that a state in which part of the first engagement portion 83*a* abuts on part of the second engagement portion 83*b* is maintained in a state before the first engagement portion 83*a* and the second engagement portion 83*b* are engaged. As a result, the operator can easily insert the claw portion 832*a* into the insertion portion 833*b* of the second groove portion 832*b* when the first engagement portion 83*a* is engaged with the second engagement portion 83*b*.

In the first modification, the film material constituting the fluid storage portion 73 is preferably joined to the vicinity of the outer peripheral end portion on the proximal side of the first valve body 71*a* and the vicinity of the outer peripheral end portion on the distal side of the second valve body 71*b*, for example, as illustrated in FIG. 14A. As a result, when engagement is performed in the first securing and holding member 83, the film material does not interfere with relative movement of the first valve body 71*a* and the second valve body 71*b*, so that it is possible to smoothly perform engagement in the first securing and holding member 83.

As illustrated in FIG. 14A, the first valve body 71*a* and the second valve body 71*b* are separated from each other as illustrated in the drawing, for example, when the gas stored in the fluid storage portion 73 is degassed to the outside. In a case where the first valve body 71*a* and the second valve body 71*b* are brought into close contact with each other again after the gas is degassed, the first valve body 71*a* is brought close to the second valve body 71*b* as illustrated in FIG. 14B. In this event, the end surface of the first valve body 71*a* and the end surface of the second valve body 71*b* are in close contact with each other, and the claw portion
832a of the first engagement portion 83a is inserted into the
insertion portion 833b of the second groove portion 832b of
the second engagement portion 83b. In the state of FIG. 14B,
the first engagement portion 83a and the second engagement
portion 83b are not yet engaged. Then, as illustrated in FIG.
14C, the first valve body 71a is relatively rotationally moved
with respect to the second valve body 71b to engage the first
engagement portion 83a and the second engagement portion
83b. As illustrated in FIG. 14C, when the first engagement
portion 83a and the second engagement portion 83b are
engaged, the claw portion 832a is engaged with the guide
portion 834b of the second groove portion 832b. As a result,
the first valve body 71a and the second valve body 71b are
engaged with each other to maintain a close contact state.

The first securing and holding member 83 only needs to
be able to hold (secure) the first valve body 71a and the
second valve body 71b in a state of being in close contact
with each other, and thus, structures of the first engagement
portion 83a and the second engagement portion 83b may be
interchanged. In addition, the first valve body 71a and the
second valve body 71b may be arranged such that, in a state
before the first engagement portion 83a and the second
engagement portion 83b are engaged, part of the first
engagement portion 83a abuts on part of the second engage-
ment portion 83b as illustrated in FIG. 14, but part of the first
engagement portion 83a does not have to abut on part of the
second engagement portion 83b. Furthermore, the joining
position of the film material constituting the fluid storage
portion 73 with respect to the first valve body 71a and the
second valve body 71b is not limited to the vicinity of the
outer peripheral end portion on the proximal side of the first
valve body 71a and the vicinity of the outer peripheral end
portion on the distal side of the second valve body 71b and
only requires to be the outer peripheral surfaces of the first
valve body 71a and the second valve body 71b.

The second securing and holding member 84 holds the
third valve body 72a and the fourth valve body 72b in a state
of being in close contact with each other. As illustrated in
FIGS. 15A to 15C, the second securing and holding member
84 includes a third engagement portion 84a provided at the
outer peripheral end portion on the distal side of the first
valve body 71a and a fourth engagement portion 84b
provided at the outer peripheral end portion on the proximal
side of the second valve body 71b.

The third engagement portion 84a is engaged with the
fourth engagement portion 84b. As an example, the third
engagement portion 84a includes a base portion 841a pro-
truding from the outer peripheral end portion on the proxi-
mal side of the third valve body 72a toward the fourth valve
body 72b, and a claw portion 842a formed in a hook shape
by bending the distal side of the base portion 841a in a
direction orthogonal to the long axis (axial) direction of the
injection member 50.

The fourth engagement portion 84b is engaged with the
third engagement portion 84a. As an example, the fourth
engagement portion 84b is provided along the outer periph-
eral end portion on the distal side of the fourth valve body
72b and is constituted by a recessed groove including a third
groove portion 841b that is engaged with the base portion
841a when engaged with the third engagement portion 84a,
and a fourth groove portion 842b that is engaged with the
claw portion 842a when engaged with the third engagement
portion 84a with a groove depth deeper than the third groove
portion 841b. The fourth groove portion 842b has an inser-
tion portion 843b into which the claw portion 842a is to be
inserted. In addition, the fourth groove portion 842b has a guide portion 844b that guides movement of the claw
portion 842a when the third valve body 72a is relatively
moved (rotational movement along the circumferential
direction) with respect to the fourth valve body 72b in a state
where the claw portion 842a is inserted into the insertion
portion 843b. The insertion portion 843b extends in the
thickness direction in the fourth valve body 72b, and the
guide portion 844b extends from a terminal end portion (butt
portion) of the insertion portion 843b along the outer periph-
eral direction of the fourth valve body 72b by a predeter-
mined length.

In addition, the third valve body 72a and the fourth valve
body 72b are preferably disposed so as to maintain a state in
which the distal portion of the claw portion 842a of the third
engagement portion 84a abuts on part of the fourth engage-
ment portion 84b in a state before the third engagement
portion 84a and the fourth engagement portion 84b are
engaged. As a result, when the third engagement portion 84a
and the fourth engagement portion 84b are engaged, the
operator can smoothly insert the claw portion 842a into the
insertion portion 843b of the fourth groove portion 842b.

In the first modification, the film material constituting the
fluid storage portion 73 is preferably joined to the vicinity of
the outer peripheral end portion on the distal side of the third
valve body 72a and the vicinity of the outer peripheral end
portion on the proximal side of the fourth valve body 72b,
for example, as illustrated in FIG. 15A. As a result, when
engagement is performed in the second securing and holding
member 84, the film material does not interfere with relative
movement of the third valve body 72a and the fourth valve
body 72b, so that it is possible to smoothly perform engage-
ment in the second securing and holding member 84.

As illustrated in FIG. 15A, for example, in a case where
the gas in the inflatable member 30 is degassed, the third
valve body 72a and the fourth valve body 72b are separated
from each other as illustrated in the drawing. In a case where
the third valve body 72a and the fourth valve body 72b are
brought into close contact with each other again after a
predetermined amount of gas flows in the fluid storage
portion 73, the third valve body 72a is brought close to the
fourth valve body 72b as illustrated in FIG. 15B. In this
event, the end surface of the third valve body 72a and the
end surface of the fourth valve body 72b are in close contact
with each other, and the claw portion 842a of the third
engagement portion 84a is inserted into the insertion portion
843b of the fourth groove portion 842b of the fourth
engagement portion 84b. In the state of FIG. 15B, the third
engagement portion 84a and the fourth engagement portion
84b are not yet engaged. Then, as illustrated in FIG. 15C, the
third valve body 72a is relatively rotationally moved with
respect to the fourth valve body 72b to engage the third
engagement portion 84a and the fourth engagement portion
84b. As illustrated in FIG. 15C, when the third engagement
portion 84a and the fourth engagement portion 84b are
engaged with each other, the claw portion 842a is engaged
with the guide portion 844b of the fourth groove portion
842b. This results in engaging the third valve body 72a and
the fourth valve body 72b and maintain a close contact state.

The second securing and holding member 84 only needs
to be able to hold (secure) the third valve body 72a and the
fourth valve body 72b in a state of being in close contact
with each other, and thus, configurations of the third engage-
ment portion 84a and the fourth engagement portion 84b
may be interchanged. In addition, the third valve body 72a
and the fourth valve body 72b may be arranged such that, in
a state before the third engagement portion 84a and the
fourth engagement portion 84b are engaged, part of the third engagement portion 84*a* abuts on part of the fourth engagement portion 84*b* as illustrated in FIG. 15, but part of the third engagement portion 84*a* does not have to abut on part of the fourth engagement portion 84*b*. Furthermore, the joining position of the film material constituting the fluid storage portion 73 with respect to the third valve body 72*a* and the fourth valve body 72*b* is not limited to the vicinity of the outer peripheral end portion on the distal side of the third valve body 72*a* and the vicinity of the outer peripheral end portion on the proximal side of the fourth valve body 72*b* and only requires to be the outer peripheral surfaces of the third valve body 72*a* and the fourth valve body 72*b*.

The hemostatic device 100 of the first modification has a configuration in which the first engagement portion 83*a* provided on the first valve body 71*a* and the second engagement portion 83*b* provided on the second valve body 71*b* are engaged by relative rotational movement of the first valve body 71*a* and the second valve body 71*b*. In addition, the hemostatic device 100 of the first modification has a configuration in which the third engagement portion 84*a* provided on the third valve body 72*a* and the fourth engagement portion 84*b* provided on the fourth valve body 72*b* are engaged by the relative rotational movement of the third valve body 72*a* and the fourth valve body 72*b*. Thus, in the hemostatic device 100 of the first modification, the closed states of the first valve member 71 and the second valve member 72 are reliably maintained, and even if the first valve member 71 and the second valve member 72 come into contact with another surrounding member (such as a desk, a bed and an indoor wall), the closed states of the first valve member 71 and the second valve member 72 are not released by the action of the first securing and holding member 83 and the second securing and holding member 84. Thus, in the hemostatic device 100 of the first modification, unintended degassing operation, or the like, does not occur, and the compressive force on the puncture site by the inflatable member 30 can be appropriately maintained.

Second Modification

Next, the second modification of the hemostatic device 100 will be described with reference to FIGS. 16A and 16B. The first securing and holding member 85 and the second securing and holding member 86 of the hemostatic device 100 of the second modification are not in a physical engagement form as in the first securing and holding member 81 and the second securing and holding member 82 in the above-described embodiment or the first securing and holding member 83 and the second securing and holding member 84 in the first modification, but in an engagement form using magnetic force.

In the hemostatic device 100 of the second modification, the first securing and holding member 85 is configured to maintain a close contact state between the first valve body 71*a* and the second valve body 71*b* by magnetic force. The second securing and holding member 86 is configured to maintain a close contact state between the third valve body 72*a* and the fourth valve body 72*b* by magnetic force.

Figure 16A:
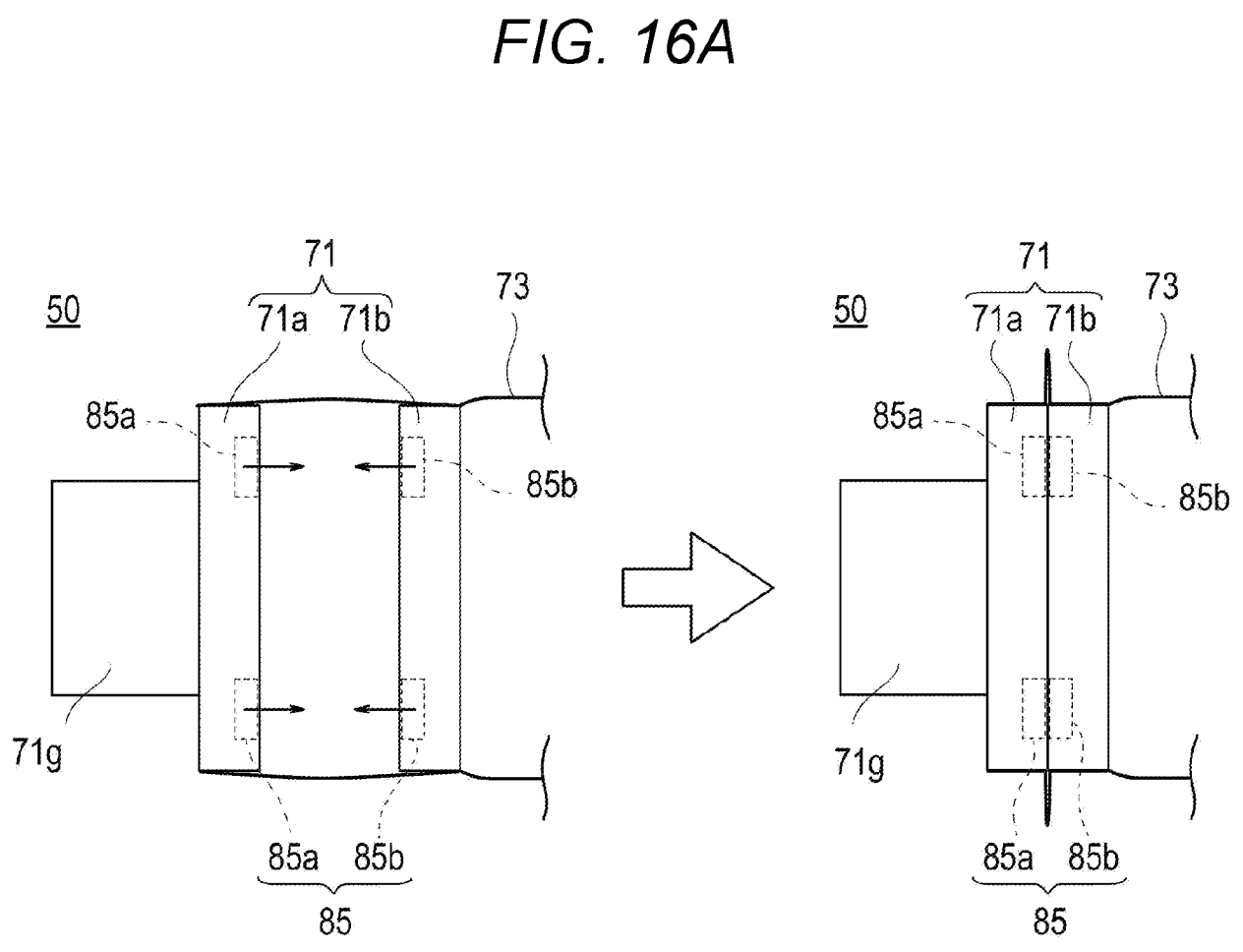

More specifically, as illustrated in FIG. 16A, the first securing and holding member 85 includes a first engagement portion 85*a* provided on the end surface on the distal side of the first valve body 71*a* and a second engagement portion 85*b* provided at a position facing the first engagement portion 85*a* with respect to the end surface on the proximal side of the second valve body 71*b*.

The first engagement portion 85*a* and the second engagement portion 85*b* are made of a magnetically connectable magnetic material such as a magnetic body and a magnet, for example. The constituent material from which the first engagement portion 85*a* may be fabricated can be appropriately selected according to a form of the second engagement portion 85*b*. In other words, in a case where the second engagement portion 85*b* is made of a magnetic body, the first engagement portion 85*a* may be made of a magnet so as to be connectable to the second engagement portion 85*b*. Further, in a case where the second engagement portion 85*b* is made of a magnet, the first engagement portion 85*a* may be made of a magnetic body or a magnet having a magnetic pole different from that of the second engagement portion 85*b* so as to be connectable to the second engagement portion 85*b*. The number and shape of the first engagement portion 85*a* and the second engagement portion 85*b* are not particularly limited as long as they can be magnetically connected to each other.

Figure 16B:
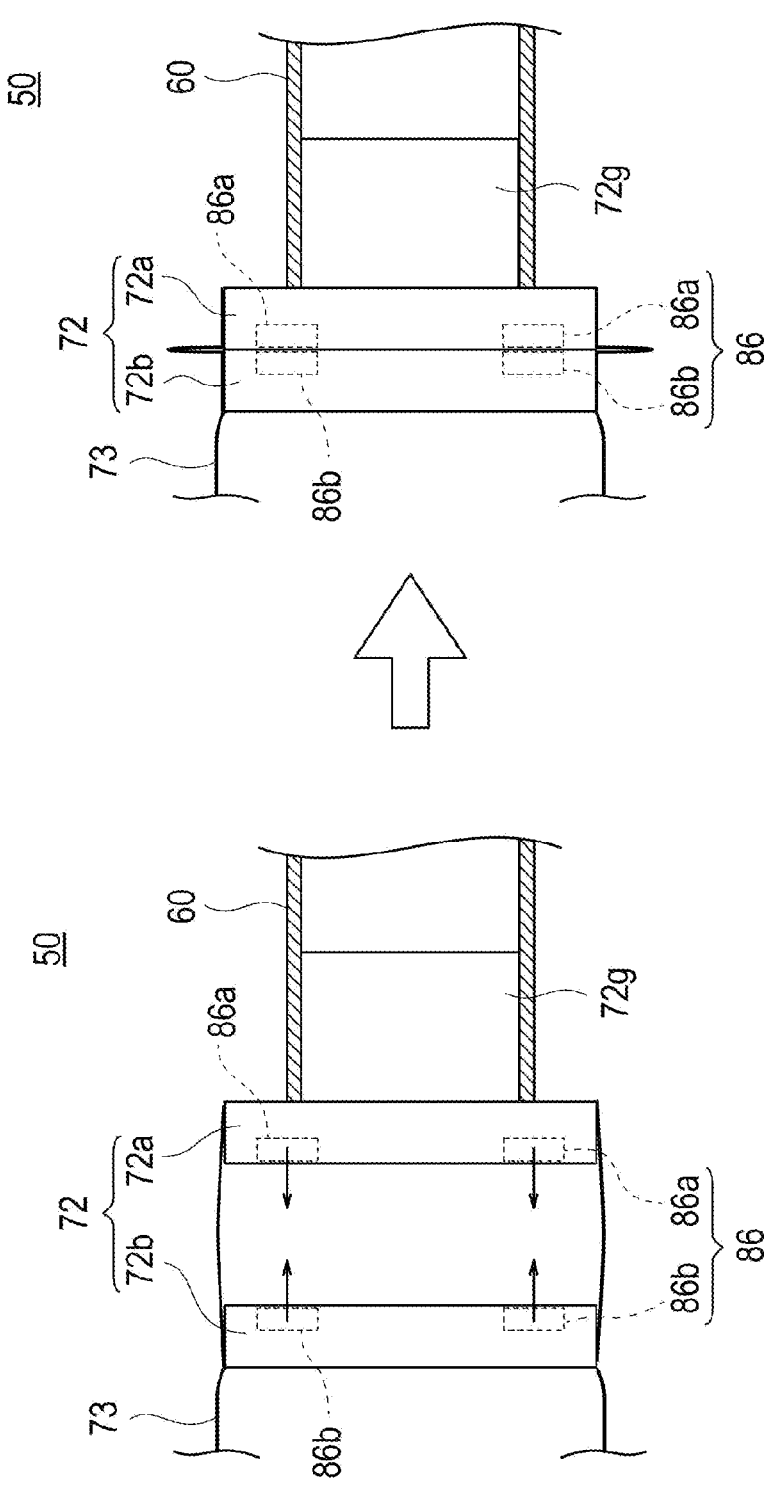
FIG. 16B is a view illustrating a configuration of a second valve member including a second securing and holding member in the hemostatic device according to the second modification.

As illustrated in FIG. 16B, the second securing and holding member 86 includes a third engagement portion 86*a* provided on the end surface on the proximal side of the third valve body 72*a* and a fourth engagement portion 86*b* provided at a position facing the third engagement portion 86*a* with respect to the end surface on the distal side of the fourth valve body 72*b*.

The third engagement portion 86*a* and the fourth engagement portion 86*b* are made of a magnetically connectable magnetic material such as a magnetic body and a magnet, for example. The constituent material from which the third engagement portion 86*a* may be fabricated can be appropriately selected according to a form of the fourth engagement portion 86*b*. In other words, in a case where the fourth engagement portion 86*b* is made of a magnetic body, the third engagement portion 86*a* may be made of a magnet so as to be connectable to the fourth engagement portion 86*b*. Further, in a case where the fourth engagement portion 86*b* is made of a magnet, the third engagement portion 86*a* may be made of a magnetic body or a magnet having a magnetic pole different from that of the fourth engagement portion 86*b* so as to be connectable to the fourth engagement portion 86*b*. The number and shape of the third engagement portion 86*a* and the fourth engagement portion 86*b* are not particularly limited as long as they can be magnetically connected to each other.

As illustrated in FIG. 16A, if the first valve body 71*a* and the second valve body 71*b* are brought close to each other, magnetic force acts to connect the first engagement portion 85*a* and the second engagement portion 85*b*, and the first valve member 71 is maintained in the closed state. Further, if the first valve body 71*a* and the second valve body 71*b* are separated against the magnetic force, both the first hole 71*d* and the second hole 71*e* are opened, whereby the first valve member 71 is in an open state. As illustrated in FIG. 16B, if the third valve body 72*a* and the fourth valve body 72*b* are brought close to each other, magnetic force acts to connect the third engagement portion 86*a* and the fourth engagement portion 86*b*, and the second valve member 72 is maintained in the closed state. Further, if the third valve body 72*a* and the fourth valve body 72*b* are separated against the magnetic force, both the third hole 72*d* and the fourth hole 72*e* are opened, whereby the second valve member 72 is in an open state.

The hemostatic device 100 of the second modification has a configuration in which the first engagement portion 85*a* and the second engagement portion 85*b* constituting the first securing and holding member 85 are magnetically connected to maintain the closed state of the first valve member 71, and the third engagement portion 86*a* and the fourth engagement portion 86b constituting the second securing and holding member 86 are magnetically connected to maintain the closed state of the second valve member 72. Thus, a configuration of the first securing and holding member 85 and the second securing and holding member 86 for maintaining the connected state is not complicated and simple, and the switching of states between the open state and the closed state of the first valve member 71 and the second valve member 72 is simple only by the simple approaching/separating operation. In addition, in the hemostatic device 100 of the second modification, the closed states of the first valve member 71 and the second valve member 72 are reliably maintained by the first securing and holding member 85 and the second securing and holding member 86, and thus, even if the hemostatic device 100 comes into contact with another surrounding member (such as a desk, a bed and an indoor wall), the closed states of the first valve member 71 and the second valve member 72 are not released by action of the first securing and holding member 85 and the second securing and holding member 86. Thus, in the hemostatic device 100 of the second modification, unintended degassing operation, or the like, does not occur, so that it is possible to appropriately maintain a compressive force on the puncture site by the inflatable member 30.

Third Modification

Figure 17A:
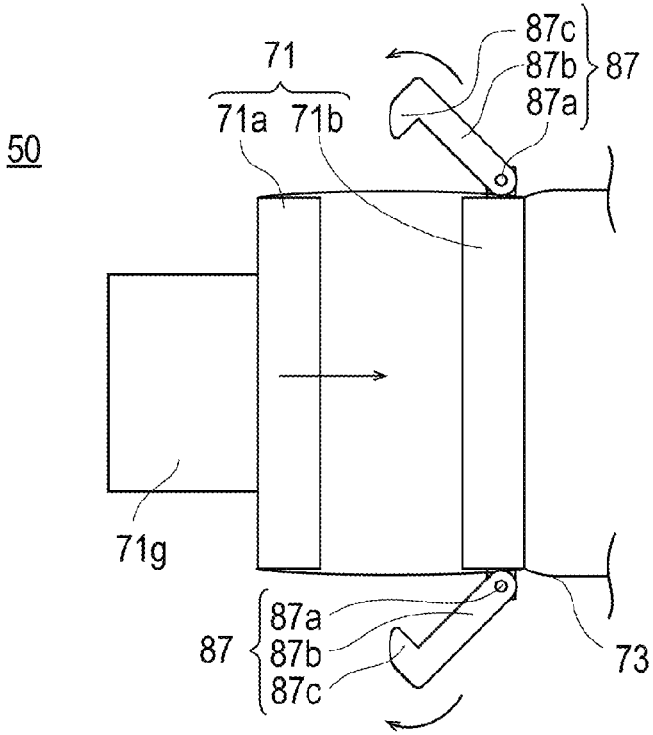
FIG. 17A is a view illustrating a state before engagement of a third securing and holding member in a hemostatic device according to a third modification.
Figure 17B:
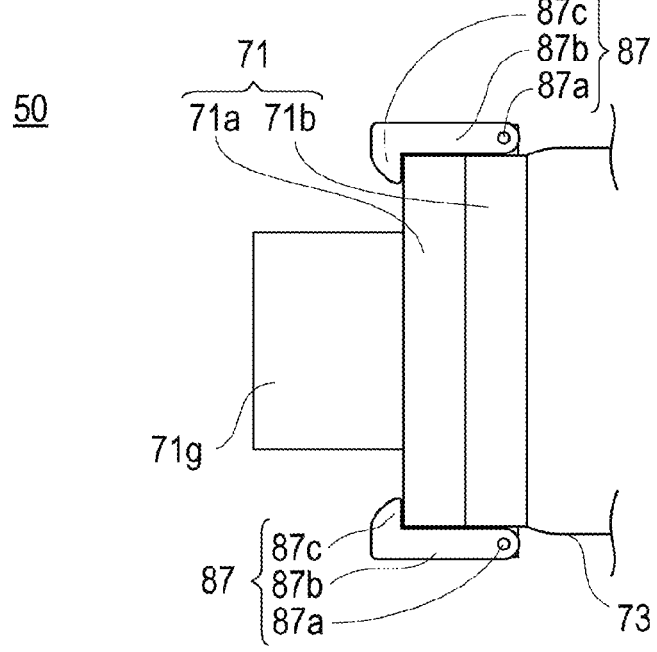
FIG. 17B is a view illustrating a state after engagement of the third securing and holding member in the hemostatic device according to the third modification.

Next, the third modification of the hemostatic device 100 will be described with reference to FIGS. 17A and 17B. The hemostatic device 100 of the third modification includes a third securing and holding member 87 as illustrated in FIGS. 17A and 17B in order to maintain closed states of the first valve member 71 and the second valve member 72. FIG. 17 illustrates a mode in which a plurality of (two in the drawing) third securing and holding members 87 is provided with respect to the first valve member 71.

The securing and holding member 80 (first securing and holding members 81, 83, and 85, second securing and holding members 82, 84, and 86) described in the above-described embodiment, first modification and second modification is constituted by members that engage with each other having different shapes or properties with respect to each of two valve bodies constituting the first valve member 71 (or the second valve member 72). On the other hand, the third securing and holding member 87 described in the third modification has a configuration in which two valve bodies constituting the first valve member 71 (or the second valve member 72) are held by one type of member.

As illustrated in FIGS. 17A and 17B, the third securing and holding member 87 is provided to be rotatable about a support shaft 87a along a direction orthogonal to the long axis (axial) direction of the injection member 50 with respect to the outer peripheral surface of the second valve body 71b. The third securing and holding member 87 includes a base portion 87b that is rotatably supported with respect to the support shaft 87a, and a hook-shaped claw portion 87c that is provided on the distal side of the base portion 87b and abuts on an end surface on the proximal side of the first valve body 71a.

A plurality of (two) third securing and holding members 87 is provided on the outer peripheral surface of the second valve body 71b. The first valve member 71 can stably maintain the closed state because a plurality of positions or locations of the end surface of the first valve body 71a is secured by providing a plurality of the third securing and holding members 87.

The third securing and holding member 87 can bring the claw portion 87c close to or away from the first valve member 71 by rotating with the support shaft 87a as a fulcrum. In a case where the first valve body 71a and the second valve body 71b are in an open state, as illustrated in FIG. 17A, the base portion 87b is rotated so as to separate the claw portion 87c from the first valve body 71a to release the engagement state. Accordingly, the movement of the first valve body 71a is not restricted by the third securing and holding member 87, and thus, the first valve body 71a can be brought close to or separated from the second valve body 71b.

In a case of maintaining the closed state of the first valve body 71a and the second valve body 71b, as illustrated in FIG. 17B, the base portion 87b is rotated so as to bring the claw portion 87c close to the first valve body 71a, and the claw portion 87c is hooked and engaged with the end surface on the proximal side of the first valve body 71a. The claw portion 87c is engaged with the end surface of the first valve body 71a to restrict the movement, and thus, the close contact state between the first valve body 71a and the second valve body 71b is maintained.

The third securing and holding member 87 is rotatably provided in the second valve body 71b in the embodiment illustrated in FIGS. 17A and 17B, but may be rotatably supported with respect to the first valve body 71a. In addition, although the embodiment illustrated in FIGS. 17A and 17B has a configuration in which a plurality of third securing and holding members 87 is provided with respect to the first valve member 71, even a single one of the third securing and holding members 87 can perform the function. Furthermore, in a case where a plurality of third securing and holding members 87 is provided, it is preferable to arrange the third securing and holding members 87 at equal intervals in the circumferential direction of the first valve member 71 so that a force is uniformly applied to the end surface of the first valve body 71a. As a result, the securing positions by the third securing and holding members 87 are arranged without bias with respect to the circumferential direction of the first valve body 71a, and the closed state of the first valve member 71 can be more stably maintained.

Although not illustrated, the third securing and holding member 87 can also be provided in the second valve member 72. By providing the third securing and holding member 87 on the fourth valve body 72b (or the third valve body 72a), the closed state of the second valve member 72 can be maintained similarly to the first valve member 71.

The hemostatic device 100 of the third modification includes the third securing and holding member 87 rotatably supported with respect to the support shaft 87a along a direction orthogonal to the long axis (axial) direction of the injection member 50 with respect to the first valve member 71 and the second valve member 72, and has a configuration of maintaining the closed states of the first valve member 71 and the second valve member 72. Thus, when the states of the first valve member 71 and the second valve member 72 are switched between the open state and the closed state, it is only necessary fort the third securing and holding member 87 to be rotated in a predetermined direction to engage or separate the claw portion 87c, and the switching operation is simple. In addition, in the hemostatic device 100 of the third modification, the closed states of the first valve member 71 and the second valve member 72 are reliably maintained by the third securing and holding member 87, and thus, even if the hemostatic device 100 comes into contact with another surrounding member (such as a desk, a bed and an indoor wall), the closed states of the first valve member 71 and the second valve member 72 are not released by action of the third securing and holding member 87. Thus, in the hemostatic device 100 of the third modification, unintended degassing operation, or the like, does not occur, so that it is possible to appropriately maintain the compressive force on the puncture site by the inflatable member 30.

As described above, the hemostatic device 100 according to the present embodiment includes the inflatable member 30 configured to compress the puncture site of the patient, the band body 10 and the hook-and-loop fastener 20 functioning as a securing member configured to secure the inflatable member 30 to the puncture site of the patient, and the injection member 50 configured to be able to inject gas (fluid) into the lumen of the inflatable member 30. In addition, the injection member 50 includes the connector portion (first protruding portion 71g) for injecting gas, the tube 60 that connects the connector portion and the lumen of the inflatable member 30, and the control unit 70 that controls flow of gas through the lumen of the injection member 50. The control unit 70 includes the first valve member 71, the second valve member 72 located closer to the inflatable member 30 than the first valve member 71, and the fluid storage portion 73 located between the first valve member 71 and the second valve member 72.

The hemostatic device 100 includes the injection member 50 including the control unit 70 having the first valve member 71, the second valve member 72, and the fluid storage portion 73 located between the first valve member 71 and the second valve member 72. The control unit 70 can store a predetermined amount of gas in the fluid storage portion 73 and reinject the gas stored in the fluid storage portion 73 into the inflatable member 30 by operating the first valve member 71 and the second valve member 72. In other words, the control unit 70 has a function equivalent to that of a dedicated instrument such as the syringe S for degassing and reinjecting gas from and into the inflatable member 30. Thus, when decompressing the inflatable member 30, the operator operates the open/closed states of the first valve member 71 and the second valve member 72 to cause part of the fluid stored in the inflatable member 30 to flow to the fluid storage portion 73, so that the fluid can be discharged from the inflatable member 30. In addition, when the fluid is reinjected into the inflatable member 30, the operator operates the open/closed states of the first valve member 71 and the second valve member 72 to cause a predetermined amount of the fluid stored in the fluid storage portion 73 to flow to the inflatable member 30, thereby injecting the fluid into the inflatable member 30. In this manner, the hemostatic device 100 can perform the decompression operation and the fluid reinjection operation on the inflatable member 30 with simple operation without using a dedicated instrument separate from the hemostatic device 100. Thus, the hemostatic device 100 can reduce labor of the operator's degassing operation and reinjection operation on the inflatable member 30.

Furthermore, the hemostatic device 100 according to the present embodiment may suitably have the following configuration. In other words, the fluid storage portion 73 may be made of a material having more flexibility than the material of the tube 60, and the fluid storage portion may be configured to expand an outer shape of the fluid storage portion 73 when the fluid is stored in the fluid storage portion 73.

It is sufficient that the fluid storage portion 73 can store a predetermined amount of fluid, and thus, for example, a tube-type configuration made of a material having no inflating function can also be adopted. However, in a case where such a tube type configuration is adopted, a certain size (length, inner diameter) is required to store a predetermined amount of gas, and there is a case where the injection member 50 may become long in the longitudinal direction, which may become an obstacle to degassing operation, or the like. In contrast, in the hemostatic device 100, the fluid storage portion 73 is configured to be inflatable, and thus, a predetermined amount of gas can be stored in a small space by shortening the length in the longitudinal direction of the injection member 50, so that it is possible to improve operability without disturbing the degassing operation, or the like. In addition, the amount of gas that can be degassed at one time can be adjusted by inflating the fluid storage portion 73, so that it is possible to reduce the number of times of degassing operation. Furthermore, the fluid storage portion 73 is made of a material having more flexibility than the material of the tube 60, and thus, the gas amount that can be stored in the fluid storage portion 73 can be temporarily increased by increasing the interval between the first valve member 71 and the second valve member 72. As a result, the amount of gas that can be degassed at one time can be adjusted in the fluid storage portion 73, so that it is possible to reduce the number of times of degassing operation.

Furthermore, the hemostatic device 100 according to the present embodiment may suitably have the following configuration. In other words, the fluid storage portion 73 may have a bellows structure capable of extending the interval between the first valve member 71 and the second valve member 72 along the longitudinal direction (long axis (axial) direction) of the control unit 70.

The fluid storage portion 73 has the bellows structure, and thus, the fluid storage portion 73 can be easily extended until the interval between the first valve member 71 and the second valve member 72 reaches a predetermined length by pulling the first valve member 71 or the second valve member 72 along the longitudinal direction of the control unit 70. Thus, when the operator performs degassing operation on the inflatable member 30, the operator can easily adjust the amount of gas that can be stored in the fluid storage portion 73. In addition, when the amount of flow from the inflatable member 30 decreases, the fluid storage portion 73 can inflate the bellows structure to extend the distance between the first valve member 71 and the second valve member 72 and generate a negative pressure in the fluid storage portion 73. Thus, the hemostatic device 100 can forcibly remove a predetermined amount of gas from the inflatable member 30, so that it is possible to continuously discharge the predetermined amount of gas from the inflatable member 30 according to a decompression protocol, or the like, without being affected by the internal pressure of the inflatable member 30.

Furthermore, the hemostatic device 100 according to the present embodiment may suitably have the following configuration. In other words, the first valve member 71 may include the first valve body 71a having the first hole 71d, the second valve body 71b having the second hole 71e and disposed at a position facing the first valve body 71a, and a deformable first connection member 71c that connects the first valve body 71a and the second valve body 71b. The second valve member 72 may include the third valve body 72a having the third hole 72d, the fourth valve body 72b having the fourth hole 72e and disposed at a position facing the third valve body 72a, and a deformable second connection member 72c that connects the third valve body 72a and the fourth valve body 72b. The first hole 71d may be arranged at a position different from the second hole 71e when the end surface of the first valve body 71a is projected onto the end surface of the second valve body 71b, and the third hole 72d may be arranged at a position different from the fourth hole 72e when the end surface of the third valve body 72a is projected onto the end surface of the fourth valve body 72b.

With such a configuration, in the first valve member 71, when the first valve body 71a and the second valve body 71b are brought into close contact with each other, the first hole 71d and the second hole 71e are closed to be in a closed state, and when the first valve body 71a and the second valve body 71b are separated from each other, the first hole 71d and the second hole 71e are opened to be in an open state. In the second valve member 72, when the third valve body 72a and the fourth valve body 72b are brought into close contact with each other, the third hole 72d and the fourth hole 72e are closed to be in a closed state, and when the third valve body 72a and the fourth valve body 72b are separated from each other, the third hole 72d and the fourth hole 72e are opened to be in an open state. Thus, the operator does not need to perform complicated operation and can switch the states of the first valve member 71 and the second valve member 72 between the open state and the closed state with simple operation. Thus, according to the hemostatic device 100, it is possible to further reduce labor of the operator's degassing operation and reinjection operation on the inflatable member 30.

Furthermore, the hemostatic device 100 according to the present embodiment may suitably have the following configuration. In other words, the first valve member 71 may include the first securing and holding member 81, 83, or 85 that maintains a state in which the first valve body 71a and the second valve body 71b are in close contact with each other, and the second valve member 72 may include the second securing and holding member 82, 84, 86, or 84 that maintains a state in which the third valve body 72a and the fourth valve body 72b are in close contact with each other.

The first valve member 71 includes the first securing and holding member 81 and the second valve member 72 includes the second securing and holding member 82, so that it is possible to maintain the closed states of the first valve member 71 and the second valve member 72. Thus, when the closed states of the first valve member 71 and the second valve member 72 are maintained, the hemostatic device 100 does not require the operator to maintain the close contact state of the first valve body 71a and the second valve body 71b (the third valve body 72a and the fourth valve body 72b) by hand or maintain the close contact state of the first valve body 71a and the second valve body 71b (the third valve body 72a and the fourth valve body 72b) by a separate body such as a clip. Thus, the hemostatic device 100 can reliably maintain the closed states of the first valve member 71 and the second valve member 72 with a simple structure, and even if the hemostatic device 100 comes into contact with another surrounding member (such as a desk, a bed and an indoor wall), the closed states of the first valve member 71 and the second valve member 72 are not released by action of the first securing and holding member 81 and the second securing and holding member 82. Thus, in the hemostatic device 100, unintended degassing operation, or the like, does not occur, and a compressive force on the puncture site by the inflatable member 30 can be appropriately maintained.

Furthermore, the hemostatic device 100 according to the present embodiment may suitably have the following configuration. In other words, the first securing and holding member 81 (or 83) may include the first engagement portion 81a (or 83a) provided at an end portion of the first valve body 71a facing the second valve body 71b and the second engagement portion 81b (or 83b) provided at an end portion of the second valve body 71b facing the first valve body 71a and engaged with the first engagement portion 81a (or 83a). The second securing and holding member 82 (or 84) may include the third engagement portion 82a (or 84a) provided at an end portion of the third valve body 72a facing the fourth valve body 72b and the fourth engagement portion 82b (or 84b) provided at an end portion of the fourth valve body 72b facing the third valve body 72a and engaged with the third engagement portion 82a (or 84a). The first engagement portion 81a (or 83a) and the second engagement portion 81b (or 83b) may be configured to be engaged by relative movement between the first valve body 71a and the second valve body 71b in a state where the first valve body 71a and the second valve body 71b are in close contact, and the third engagement portion 82a (or 84a) and the fourth engagement portion 82b (or 84b) may be configured to be engaged by relative movement between the third valve body 72a and the fourth valve body 72b in a state where the third valve body 72a and the fourth valve body 72b are in close contact.

In order to maintain the closed state of the first valve member 71, the hemostatic device 100 includes the first engagement portion 81a (or 83a) and the second engagement portion 81b (or 83b) that relatively move and engage the first valve body 71a and the second valve body 71b in a state where the first valve body 71a and the second valve body 71b are in close contact with each other. In addition, in order to maintain the closed state of the second valve member 72, the hemostatic device 100 includes the third engagement portion 82a (or 84a) and the fourth engagement portion 82b (or 84b) that relatively move and engage the third valve body 72a and the fourth valve body 72b in a state where the third valve body 72a and the fourth valve body 72b are in close contact with each other. Thus, the operator can reliably maintain the closed state of the first valve member 71 or the second valve member 72 by simple operation of relatively moving the first valve body 71a and the second valve body 71b or relatively moving the third valve body 72a and the fourth valve body 72b. Thus, even if the hemostatic device 100 comes into contact with another surrounding member (such as a desk, a bed and an indoor wall), the closed states of the first valve member 71 and the second valve member 72 are not released by the action of the first securing and holding member 81 (or 83) and the second securing and holding member 82 (or 84). Thus, in the hemostatic device 100, unintended degassing operation, or the like, does not occur, and a compressive force on the puncture site by the inflatable member 30 can be appropriately maintained.

Furthermore, the hemostatic device 100 according to the present embodiment may suitably have the following configuration. In other words, the first securing and holding member 85 may include the first engagement portion 85a made of a magnetic material and provided on the end surface of the first valve body 71a facing the second valve body 71b, and the second engagement portion 85b made of a magnetic material and provided on the end surface of the second valve body 71b facing the first valve body 71a and magnetically connected to the first engagement portion 85a. The second securing and holding member 86 may include the third engagement portion 86a made of a magnetic material and provided on the end surface of the third valve body 72a facing the fourth valve body 72b, and the fourth engagement portion 86b made of a magnetic material and provided on the end surface of the fourth valve body 72*b* facing the third valve body 72*a* and magnetically connected to the third engagement portion 86*a*.

In the hemostatic device 100, the first valve member 71 includes the first securing and holding member 85 including the magnetically connectable first engagement portion 85*a* and the second engagement portion 85*b*, and the second valve member 72 includes the second securing and holding member 86 including the magnetically connectable third engagement portion 86*a* and the fourth engagement portion 86*b*. Thus, in the hemostatic device 100, when the states of the first valve member 71 and the second valve member 72 are switched between the open state and the closed state, the closed state of the first valve member 71 is maintained only by simply approaching/separating of the first valve body 71*a* and the second valve body 71*b*, and the closed state of the second valve member 72 is maintained only by simply approaching/separating of the third valve body 72*a* and the fourth valve body 72*b*. Thus, the hemostatic device 100 can perform gas flow control with simple configuration. Further, the hemostatic device 100 includes the first securing and holding member 85 and the second securing and holding member 86, and thus, even if the hemostatic device 100 comes into contact with another surrounding member (such as a desk, a bed and an indoor wall), the closed states of the first valve member 71 and the second valve member 72 are not released by action of the first securing and holding member 85 and the second securing and holding member 86. Thus, in the hemostatic device 100, unintended degassing operation, or the like, does not occur, and a compressive force on the puncture site by the inflatable member 30 can be appropriately maintained.

The detailed description above describes embodiments of a hemostatic device representing examples of the new hemostatic device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

REFERENCE SIGNS LIST

11 Belt
12 Support plate
20 Hook-and-loop fastener (21: male side, 22: Female side)
30 Inflatable member
31 Inflatable space
40 Marker
50 Injection member
60 Tube
70 Control unit
71 First valve member (71*a*: first valve body, 71*b*: second valve body, 71*c*: first connection member, 71*d*: first hole, 71*e*: second hole, 71*f*: first flow space, 71*g*: first protruding portion
72 Second valve member (72*a*: third valve body, 72*b*: fourth valve body, 72*c*: second connection member, 72*d*: third hole, 72*e*: fourth hole, 72*f*: second flow space, 72*g*: second protruding portion)
73 Fluid storage portion
80 Securing and holding member 81, 83, 85 First securing and holding member (81*a*, 83*a*, 85*a*: first engagement portion, 81*b*, 83*b*, 85*b*: second engagement portion)
82, 84, 86 Second securing and holding member (82*a*, 84*a*, 86*a*: third engagement portion, 82*b*, 84*b*, 86*b*: fourth engagement portion)
87 Third securing and holding member
100 Hemostatic device
R Radial artery
S Syringe
W Wrist

What is claimed is:

1. A hemostatic device comprising:
an inflatable member configured to compress a puncture site of a patient;
a securing member configured to secure the inflatable member to the puncture site of the patient;
an injection member configured to inject a fluid into a lumen of the inflatable member;
the injection member including a connector portion connectable to a fluid source to inject the fluid, a main body portion that connects the connector portion and the lumen of the inflatable member, and a control unit that controls flow of the fluid through a lumen of the injection member; and
the control unit including a first valve member, a second valve member located closer to the inflatable member than the first valve member, and a fluid storage portion located between the first valve member and the second valve member, the second valve member being configured to be switched between an open state in which fluid flow through the second valve member is permitted and a closed state in which fluid flow through the second valve member is blocked, wherein the second valve member includes two valve bodies that are relatively movable towards and away from one another to switch between the open state and the closed state of the second valve member.

2. The hemostatic device according to claim 1,
wherein the fluid storage portion is made of a material that is more flexible than a material of which the main body portion is made, and
the fluid storage portion is expandable to expand an outer shape of the fluid storage portion when the fluid is stored in the fluid storage portion.

3. The hemostatic device according to claim 1, wherein the fluid storage portion is a bellows that is axially expandable to change a distance between the first valve member and the second valve member along a longitudinal direction of the control unit.

4. The hemostatic device according to claim 1,
wherein the first valve member includes a first valve body having a first hole, a second valve body having a second hole and disposed at a position facing the first valve body, and a deformable first connection member that connects the first valve body and the second valve body,
the second valve member includes a third valve body having a third hole, a fourth valve body having a fourth hole and disposed at a position facing the third valve body, and a deformable second connection member that connects the third valve body and the fourth valve body,
the first hole is disposed at a position different from a position of the second hole when an end surface of the first valve body faces an end surface of the second valve body, and the third hole is disposed at a position different from a position of the fourth hole when an end surface of the third valve body faces an end surface of the fourth valve body.

5. The hemostatic device according to claim 4, wherein the first valve member includes a first securing and holding member that maintains a state in which the first valve body and the second valve body are in close contact with each other, and the second valve member includes a second securing and holding member that maintains a state in which the third valve body and the fourth valve body are in close contact with each other.

6. The hemostatic device according to claim 5, wherein the first securing and holding member includes a first engagement portion provided at an end portion of the first valve body facing the second valve body and a second engagement portion provided at an end portion of the second valve body facing the first valve body and engaged with the first engagement portion, the second securing and holding member includes a third engagement portion provided at an end portion of the third valve body facing the fourth valve body and a fourth engagement portion provided at an end portion of the fourth valve body facing the third valve body and engaged with the third engagement portion, the first engagement portion and the second engagement portion are configured to be engaged by relative movement between the first valve body and the second valve body in a state where the first valve body and the second valve body are brought into close contact with each other, and the third engagement portion and the fourth engagement portion are configured to be engaged by relative movement between the third valve body and the fourth valve body in a state where the third valve body and the fourth valve body are brought into close contact with each other.

7. The hemostatic device according to claim 5, wherein the first securing and holding member includes a first engagement portion made of a magnetic material and provided on an end surface of the first valve body facing the second valve body, and a second engagement portion made of a magnetic material and provided on an end surface of the second valve body facing the first valve body and magnetically connected to the first engagement portion, and the second securing and holding member includes a third engagement portion made of a magnetic material and provided on an end surface of the third valve body facing the fourth valve body, and a fourth engagement portion made of a magnetic material and provided on an end surface of the fourth valve body facing the third valve body and magnetically connected to the third engagement portion.

8. A hemostatic device comprising:

an inflatable member that is inflatable by way of fluid flowing into an interior of the inflatable member;

a band to which the inflatable member is connected, the band including first and second portions that are engageable with one another when the band is in a wrapped state on the patient to secure the band on the patient and position the inflatable member to apply a compression force to the puncture site when the inflatable member is inflated;

a first valve and a second valve that are spaced apart from one another, and a fluid storage positioned between the first valve and the second valve, the fluid storage including an interior, the first valve and the second valve being switchable between an open state and a closed state;

the first valve being connected to the fluid storage container and the inflatable member so that when the first valve is in the open state the first valve permits communication between the interior of the inflatable member and the interior of the fluid storage, and so that when the first valve is in the closed state communication between the interior of the inflatable member and the interior of the fluid storage is blocked by the first valve; and at least one of the first valve and the second valve comprising: one valve body and an other valve body that are connected to each other by a connection member, the connection member allowing relative movement between the one valve body and the other valve body to switch the at least one of the first valve and the second valve between the open state and the closed state.

9. The hemostatic device according to claim 8, wherein the first valve is connected to the fluid storage container by way of a tube that engages a projection projecting away from the first valve.

10. The hemostatic device according to claim 9, wherein the fluid storage portion is made of a material that is more flexible than a material from which the tube is made.

11. The hemostatic device according to claim 8, wherein the first valve comprises the one valve body and the other valve body, the one valve body being a first valve body, the other valve body being a second valve body, the connection member being a first connection member, the second valve comprising a third valve body and a fourth valve body that are connected to each other by a second connection member, the second connection member allowing relative movement between the third valve body and the fourth valve body to switch the second valve between the open state and the closed state.

12. The hemostatic device according to claim 8, wherein the one valve body and the other valve body each include a plate-shaped member provided with a through hole, the through hole in the one valve body possessing a central axis, the through hole in the other valve body possessing a central axis, the central axis of the through hole in the one valve body and the central axis of the through hole in the other valve body being spaced apart from one another.

13. The hemostatic device according to claim 8, wherein the connection member is a flexible film.

14. The hemostatic device according to claim 8, wherein the one valve body possesses an end surface and the other valve body possesses an end surface, the connection member being a flexible film that surrounds an interior located between the end surface of the one valve body and the end surface of the other valve body when the at least one of the first valve and the second valve is in the open position.

15. The hemostatic device according to claim 8, wherein the one valve body includes a part that engages a part of the other valve body when the at least one of the first valve and the second valve is in the closed state to maintain the at least one of the first valve and the second valve in the closed state.

16. The hemostatic device according to claim 15, wherein the part of the one valve body incudes a hook and the part of the other valve body is a recess, the hook being positionable in the recess when the at least one of the first valve and the second valve is in the closed state to maintain the at least one of the first valve and the second valve in the closed state.

17. The hemostatic device according to claim 8, wherein the one valve body and the other valve body each include magnetically connectable magnetic material causing the one valve body and the other valve body to be magnetically attracted to one another when the at least one of the first valve and the second valve is in the closed state to maintain the at least one of the first valve and the second valve in the closed state.

18. A hemostatic device comprising:

an inflatable member that is inflatable by way of fluid flowing into an interior of the inflatable member;

a band to which the inflatable member is connected, the band being wrappable around a portion of the patient in a wrapped state to position the inflatable member relative to a puncture site of the patient, the band including first and second portions that are engageable with one another when the band is in the wrapped state on the patient to secure the band on the patient and position the inflatable member to apply a compression force to the puncture site when the inflatable member is inflated;

a first valve and a second valve that are spaced apart from one another and that are axially movable relative to one another, and a fluid storage positioned between the first valve and the second valve, the fluid storage being joined to the first valve and the second valve so that an interior of the fluid storage is sealed, each of the first valve and the second valve being switchable between an open state in which fluid flow is permitted and a closed state in which fluid flow is prevented;

the first valve having one end in communication with the interior of the inflatable member and an opposite end in communication with the interior of the fluid storage, the second valve having one end connectable to a source of the fluid and an opposite end in communication with the interior of the fluid storage; and the fluid storage that is positioned between the first valve and the second valve being constructed to permit the first valve and the second valve to axially move relative to one another.

19. The hemostatic device according to claim 18, wherein the fluid storage is either an inflatable film material or a bellows structure.

20. The hemostatic device according to claim 18, wherein the one end of the first valve is connected to a tube, the tube also being connected to the inflatable member to provide the communication between the one end of the first valve and the interior of the inflatable member, the fluid storage being made of a material that is more flexible than material from which the tube is made.

* * * * *